United States Patent
Raskin et al.

(10) Patent No.: US 11,147,847 B2
(45) Date of Patent: Oct. 19, 2021

(54) EXTRACTS FROM PLANTS OF THE MORINGACEAE FAMILY AND METHODS OF MAKING

(71) Applicant: Rutgers, The State University of New Jersey, New Brunswick, NJ (US)

(72) Inventors: Ilya Raskin, Manalapan, NJ (US); Carrie Waterman, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 438 days.

(21) Appl. No.: 14/683,730

(22) Filed: Apr. 10, 2015

(65) Prior Publication Data

US 2015/0209395 A1 Jul. 30, 2015

Related U.S. Application Data

(63) Continuation-in-part of application No. PCT/US2014/063178, filed on Oct. 30, 2014.

(60) Provisional application No. 62/032,496, filed on Aug. 1, 2014, provisional application No. 61/898,795, filed on Nov. 1, 2013.

(51) Int. Cl.
| | |
|---|---|
| *A61K 36/185* | (2006.01) |
| *A23L 33/125* | (2016.01) |
| *A23L 33/105* | (2016.01) |
| *A23L 33/00* | (2016.01) |
| *A61K 8/97* | (2017.01) |
| *A61Q 19/00* | (2006.01) |
| *A23K 20/10* | (2016.01) |
| *A61K 31/7034* | (2006.01) |

(52) U.S. Cl.
CPC .......... *A61K 36/185* (2013.01); *A23K 20/10* (2016.05); *A23L 33/105* (2016.08); *A23L 33/125* (2016.08); *A23L 33/30* (2016.08); *A61K 8/97* (2013.01); *A61K 31/7034* (2013.01); *A61Q 19/00* (2013.01); *A23V 2002/00* (2013.01); *A61K 2236/00* (2013.01); *A61K 2236/15* (2013.01); *A61K 2236/17* (2013.01); *A61K 2236/19* (2013.01); *A61K 2236/33* (2013.01); *A61K 2236/331* (2013.01); *A61K 2236/53* (2013.01); *A61K 2800/10* (2013.01)

(58) Field of Classification Search
None
See application file for complete search history.

(56) References Cited

U.S. PATENT DOCUMENTS

| | | | | |
|---|---|---|---|---|
| 2003/0235634 | A1 * | 12/2003 | Pusateri | A61K 2300/00 424/755 |
| 2004/0001896 | A1 | 1/2004 | Kuppam | |
| 2006/0127996 | A1 * | 6/2006 | Fahey | A23L 1/3002 435/128 |
| 2007/0264366 | A1 * | 11/2007 | Chen | A61K 36/185 424/769 |
| 2011/0245526 | A1 * | 10/2011 | Ekanayake | C12P 11/00 558/13 |
| 2012/0052175 | A1 * | 3/2012 | Ekanayake | C11B 9/025 426/532 |

FOREIGN PATENT DOCUMENTS

| | | | |
|---|---|---|---|
| EP | 2080516 A1 * | 7/2009 | A61K 31/26 |
| EP | 2080516 B1 | 6/2011 | |
| WO | WO-2014/053944 A1 | 4/2014 | |
| WO | WO-2015/066339 A1 | 5/2015 | |

OTHER PUBLICATIONS

Abdulkarim et al. (2005) Food Chemistry 93: 253-263.*
Anwar et al. (2007) Phytother. Res. 21, 17-25.*
Chuang et al. (2007) Bioresource Technology 98: 232-236.*
Eilert et al. (1981) J. Medicinal Plant Res. 42: 55-61.*
Fahey, J. (2005) Trees for Life Journal, 1:5.*
Okuda et al. (2001) Wat. Res. vol. 35, No. 2, pp. 405-410.*
Rockwood et al. (2013) Inter. J. Phytother. Res. vol. 3, Issue 2, 61-71.*
Oluduro et al. (2010) Folia Microbiol. 55(5): 422-426.*
Oluduro et al. (2012) Res. J. Medicinal Plant 6(5): 383-394.*
Alberti et al., Harmonizing the metabolic syndrome: a joint interim statement of the International Diabetes Federation Task Force on Epidemiology and Prevention; National Heart, Lung, and Blood Institute; American Heart Association; World Heart Federation; International Atherosclerosis Society; and International Association for the Study of Obesity, *Circulation*, 120(16): 1640-5 (2009).
Amaglo et al., Profiling selected phytochemicals and nutrients in different tissues of the multipurpose tree *Moringa oleifera* L., grown in Ghana, *Food Chem.* 122(4): 1047-54 (2010).
Bae et al., Bog blueberry anthocyanins alleviate photoaging in ultraviolet-B irradiation-induced human dermal fibroblasts, *Mol. Nutr. Food Res.* 53(6): 726-38 (2009).
Bahadoran et al., Effect of broccoli sprouts on insulin resistance in type 2 diabetic patients: a randomized double-blind clinical trial, *Int. J. Food Sci. Nutr.* 63(7): 767-71 (2012).
Bahadoran et al., Potential efficacy of broccoli sprouts as a unique supplement for management of type 2 diabetes and its complications, *J. Med. Food*, 16(5): 375-82 (2013).

(Continued)

Primary Examiner — Russell G Fiebig
(74) Attorney, Agent, or Firm — Marshall, Gerstein & Borun LLP

(57) ABSTRACT

The present application is directed to materials and methods for producing extracts from a plant of the Moringaceae family having high concentrations of *moringa* isothiocyanates.

4 Claims, 10 Drawing Sheets

Specification includes a Sequence Listing.

(56) References Cited

OTHER PUBLICATIONS

Bais et al., Antiobesity and hypolipididemic activity of Moringa oleifera leaves against high fat diet-induced obesity in rats. *Adv. Biol.* 2014: 1-9 (2014).
Bao et al., The complexities of obesity and diabetes with the development and progression of pancreatic cancer, *Biochim. Biophys. Acta*, 1815(2): 135-46 (2011).
Bennett et al., Profiling glucosinolates and phenolics in vegetative and reproductive tissues of the multi-purpose trees *Moringa oleifera* L. (horseradish tree) and *Moringa stenopetala* L. *J. Agric. Food Chem.* 51(12): 3546-53 (2003).
Bhargava et al., Role and function of macrophages in the metabolic syndrome, *Biochem. J.* 442(2): 253-62 (2012).
Brunelli et al., The isothiocyanate produced from glucomoringin inhibits NF-kB and reduces myeloma growth in nude mice in vivo, *Biochem. Pharmacol.* 79(8): 1141-8 (2010).
Cheenpracha et al., Potential anti-inflammatory phenolic glycosides from the medicinal plant *Moringa oleifera* fruits. Bioorg. Med. Chem. 18(17): 6598-602 (2010).
Cheng et al., In vivo and in vitro antidiabetic effects of aqueous cinnamon extract and cinnamon polyphenol-enhanced food matrix, *Food Chem.* 135(4): 2994-3002 (2012).
Dillard et al., Phytochemicals: Nutraceuticals and human health, *J. Sci. Food Agric.* 80(12): 1744-56 (2000).
Eilert et al., The antibiotic principle of seeds of *Moringa oleifera* and *Moringa stenopetala*, *J. Med. Plant Res.* 42: 55-61 (1981).
El Messaoudi et al., The cardioprotective effects of metformin, *Curr. Opin Lipidol.* 22(6): 445-53 (2011).
Eylen et al., Effects of pressure/temperature treatments on stability and activity of endogenous broccoli (*Brassica oleracea* L. cv. Italica) myrosinase and on cell permeability, *J. Food Engin.* 89(2): 178-186 (2008).
Fahey, *Moringa oleifera*: A review of the medical evidence for its nutritional, therapeutic, and prophylactic properties. Part 1, *Trees Life J.* 1-15 (2005).
Faizi et al., Isolation and structure elucidation of new nitrile and mustard oil glycosides from *Moringa oleifera* and their effect on blood pressure. *J. Nat. Prod.* 57(9): 1256-61 (1994).
Ferrante, Obesity-induced inflammation: A metabolic dialogue in the language of inflammation, *J. Intern. Med.* 262(4): 408-14 (2007).
Folch et al., A simple method for the isolation and purification of total lipids from animal tissues, *J. Biol. Chem.* 226(1): 497-509 (1957).
Force et al., Impact of cold storage on glucosinolate levels in seed-sprouts of broccoli, rocket, white radish and kohl-rabi, *Postharvest Biol. Technol.* 44(2): 175-8 (2007).
Gallaher et al., Development and validation of a spectrophotometric method for quantification of total glucosinolates in cruciferous vegetables, *J. Agric. Food Chem.* 60(6): 1358-62 (2012).
Geerling et al., Metformin lowers plasma triglycerides by promoting VLDL-triglyceride clearance by brown adipose tissue in mice, *Diabetes*, 63(3): 880-91 (2013).
Geronikaki et al., Antioxidants and inflammatory disease: synthetic and natural antioxidants with anti-inflammatory activity, *Comb. Chem. High Throughput Screen.*, 9(6): 425-42 (2006).
Giusti et al., Acylated anthocyanins from edible sources and their applications in food systems, *Biochem. Engin. J.* 14(3): 217-25 (2003).
Higdon et al., Cruciferous vegetables and human cancer risk: epidemiologic evidence and mechanistic basis, *Pharmacol. Res.* 55(3): 224-36 (2007).
Hobbs et al., Inhibition of nitric oxide synthase as a potential therapeutic target, *Ann. Rev. Pharmacol. Toxicol.* 39(1): 191-220 (1999).
Hotamisligil et al., Tumor necrosis factor alpha inhibits signaling from the insulin receptor, *Proc. Natl. Acad. Sci. USA*, 91(11): 4854-8 (1994).
Hundal et al., Mechanism by which metformin reduces glucose production in type 2 diabetes, *Diabetes*, 49(12): 2063-9 (2000).
International Searching Authority, Written Opinion issued in connection with PCT/US2014/063178 dated Feb. 23, 2015.
Jaiswal et al., Effect of *Moringa oleifera* Lam. leaves aqueous extract therapy on hyperglycemic rats, *J. Ethnopharmacol.* 123(3): 392-6 (2009).
Knowler et al., Reduction in the incidence of type 2 diabetes with lifestyle intervention or metformin, *New Engl. J. Med.* 346(6): 393-403 (2002).
Korda et al., Leptin-induced endothelial dysfunction in obesity, *Am. J. Physiol. Heart Circ. Physiol.* 295(4): H1514-21 (2008).
Kunyanga et al., Total phenolic content, antioxidant and antidiabetic properties of methanolic extract of raw and traditionally processed Kenyan indigenous food ingredients. *LWT Food Sci. Tech.* 45: 269-76 (2012).
Madiraju et al., Metformin suppresses gluconeogenesis by inhibiting mitochondrial glycerophosphate dehydrogenase, *Nature*, 510: 542-6 (2014).
Mariappan et al., NF-kappaB-induced oxidative stress contributes to mitochondrial and cardiac dysfunction in type II diabetes, *Cardio. Res.* 85(3): 473-83 (2010).
Mbanya et al., Diabetes in sub-Saharan Africa, *Lancet*, 375(9733): 2254-66 (2010).
Mbikay, Therapeutic potential of *Moringa oleifera* leaves in chronic hyperglycemia and dyslipidemia: a review, *Front Pharmacol.* 3(24): 1-12 (2012).
Mekonnen, Effects of ethanol extract of Moringa stenopetala leaves on guinea-pig and mouse smooth muscle. *Phytother. Res.* 13: 442-44 (19991).
Miller et al., Adipocyte gene expression is altered in formerly obese mice and as a function of diet composition, *J. Nutr.* 138(6): 1033-8 (2008).
Mirmiran et al., Effects of broccoli sprout with high sulforaphane concentration on inflammatory markers in type 2 diabetic patients: A randomized double-blind placebo-controlled clinical trial. *J. Funct. Foods*, 4(4): 837-41 (2012).
Mirza et al., Type 2-diabetes is associated with elevated levels of TNF-alpha, IL-6 and adiponectin and low levels of leptin in a population of Mexican Americans: a cross-sectional study, *Cytokine*, 57(1): 136-142 (2012).
Mocellin et al., TNF and cancer: the two sides of the coin, *Front. Biosci.* 13: 2774-2783 (2008).
Moller, Potential role of TNF-alpha in the pathogenesis of insulin resistance and type 2 diabetes, *Trends Endocrin. Metab.* 11(6): 212-7 (2000).
Mosmann, Rapid colorimetric assay for cellular growth and survival: application to proliferation and cytotoxicity assays, *J Immunol Methods*, 65(1):55-63 (1983).
Moyo et al., Polyphenolic content and antioxidant properties of *Moringa oleifera* leaf extracts and enzymatic activity of liver from goats supplemented with Moringa oleifera leaves/sunflower seed cake, *Meat Science*, 91(4): 441-7 (2012).
Myrosinase—Wikipedia, https://en.wikipedia.org/wiki/Myrosinase , Jun. 29, 2017.
Ndong et al., Effects of oral administration of *Moringa oleifera* lam on glucose tolerance in Goto-Kakizaki and Wistar rats, *J. Clin. Biochem. Nutr.* 40(3): 229-33 (2007).
Ng et al., Global, regional, and national prevalence of overweight and obesity in children and adults during 1980-2013: a systematic analysis for the Global Burden of Disease Study 2013, *Lancet*, 384(9945): 776-81 (2014).
Padla et al., Antimicrobial isothiocyanates from the seeds of Moringa oleifera lam, *Z Naturforsch C*, 67(11-12): 557-64 (2012).
Pandey et al., *Moringa Oleifera* Lam. (Sahijan)—A Plant with a Plethora of Diverse Therapeutic Benefits: An Updated Retrospection Medicinal & Aromatic Plants: *Med. Aromat. Plants*, 1(1):1-8 (2012).
Park et al., Inhibition of lipopolysaccharide-induced cyclooxygenase-2 and inducible nitric oxide synthase expression by 4-[(2'-O-acetyl-α-L-rhamnosyloxy)benzyl]isothiocyanate from *Moringa oleifera*, *Nutr. Cancer*, 63(6): 971-82 (2011).

(56) References Cited

OTHER PUBLICATIONS

Pereira et al., Influence of temperature and ontogeny on the levels of glucosinolates in broccoli (*Brassica oleracea* Var. *italica*) sprouts and their effect on the induction of mammalian phase 2 enzymes, *J. Agric. Food Chem.* 50(21): 6239-44 (2002).
Prior et al., Assays for hydrophilic and lipophilic antioxidant capacity (oxygen radical absorbance capacity (ORAC(FL))) of plasma and other biological and food samples, *J. Agric. Food Chem.* 51(11): 3273-9 (2003).
Rena et al., Molecular mechanism of action of metformin: old or new insights?, *Diabetologia*, 56(9): 1898-906 (2013).
Schmittgen et al., Analyzing real-time PCR data by the comparative CT method, *Nat. Protocols*, 3(6): 1101-8 (2008).
Schreyer et al., Obesity and diabetes in TNF-alpha receptor-deficient mice, *J. Clin. Invest.* 102(2): 402-11 (1998).
Shapiro et al., Chemoprotective glucosinolates and isothiocyanates of broccoli sprouts metabolism and excretion in humans, *Cancer Epidem. Biomar.* 10(5): 501-8 (2001).
Shetty, Public health: India's diabetes time bomb, *Nature*, 485(7398): S14-S6 (2012).
Siddhuraju et al., Antioxidant properties of various solvent extracts of total phenolic constituents from three different agroclimatic origins of drumstick tree (*Moringa oleifera* Lam.) leaves, *J. Agric. Food Chem.*, 51(8): 2144-55 (2013).
Singleton et al., Colorimetry of total phenolics with phosphomolybdic-phosphotungstic acid reagents, *Am. J. Enol. Viticulture*, 16(3): 144-58 (1965).
Song et al., Effect of storage, processing and cooking on glucosinolate content of Brassica vegetables, *Food Chem. Toxicol.* 45(2): 216-24 (2007).
Sreelatha et al., Antioxidant activity and total phenolic content of *Moringa oleifera* leaves in two stages of maturity, *Plant Foods Hum. Nutr.* 64(4): 303-311 (2009).
Srinivasan et al., Combination of high-fat diet-fed and low-dose streptozotocin-treated rat: A model for type 2 diabetes and pharmacological screening, *Pharmacol. Res.* 52(4): 313-20 (2005).
Srivastava et al., Cell cycle arrest, apoptosis induction and inhibition of nuclear factor kappa B activation in anti-proliferative activity of benzyl isothiocyanate against human pancreatic cancer cells, *Carcinogenesis*, 25(9): 1701-9 (2004).
Steppan et al., The hormone resistin links obesity to diabetes, *Nature*, 409(6818): 307-12 (2001).
Traka et al., Glucosinolates, isothiocyanates and human health, *Phytochem. Rev.* 8(1): 269-82 (2009).
Uysal et al., Protection from obesity-induced insulin resistance in mice lacking TNFalpha function, *Nature*, 389(6651): 610-4 (1997).
Verhoeven et al., Epidemiological studies on brassica vegetables and cancer risk, *Cancer Epidem. Biomar.* 5(9): 733-48 (1996).
Vongsak et al., Maximizing total phenolics, total flavonoids contents and antioxidant activity of *Moringa oleifera* leaf extract by the appropriate extraction method, *Indust. Crops Prod.* 44: 566-71 (2013).
Wadsworth et al., Effects of the wine polyphenolics quercetin and resveratrol on pro-inflammatory cytokine expression in RAW 264.7 macrophages, *Biochem. Pharmacol.* 57(8): 941-9 (1999).
Wang et al., The obesity epidemic in the United States—gender, age, socioeconomic, racial/ethnic, and geographic characteristics: a systematic review and meta-regression analysis, *Epidemiol. Rev.* 29(1): 6-28 (2007).
Waterman et al., Stable, water extractable isothiocyanates from Moringa oleifera leaves attenuate inflammation in vitro, *Phytochem.* 103: 114-22 (2014).
Widjaja et al., UKPDS 20: plasma leptin, obesity, and plasma insulin in type 2 diabetic subjects, *J. Clin. Endocrinol. Metab.* 82(2): 654-7 (1997).
Wu et al., Lipophilic and hydrophilic antioxidant capacities of common foods in the United States, *J. Agric. Food Chem.* 52(12): 4026-37 (2004).
Wu et al., Preparation and stability investigation of the inclusion complex of sulforaphane with hydroxypropyl-β-cyclodextrin, *Carbohyd. Polym.* 82(3): 613-7 (2010).
Xu et al., Chronic inflammation in fat plays a crucial role in the development of obesity-related insulin resistance, *J. Clin. Invest.* 112(12): 1821-30 (2003).
Xu et al., Suppression of NF-kappaB and NF-kappaB-regulated gene expression by sulforaphane and PEITC through IkappaBalpha, IKK pathway in human prostate cancer PC-3 cells, *Oncogene*, 24(28): 4486-95 (2005).
Abdulkarim et al., Some physico-chemical properties of *Moringa oleifera* seed oil extracted using solvent and aqueous enzymatic methods. *Food Chem.* 93: 253-63 (2005).
Anwar et al., *Moringa oleifera*: A food plant with multiple medicinal uses. *Phytother. Res.* 21: 17-25 (2007).
Chuang et al., Anti-fungal activity of crude extracts and essential oil of *Moringa oleifera* lam. *Bioresource Technol.* 98: 232-6 (2007).
Dehshahri et al., Determination of volatile glucosinolate degradation products in seed coat, stem and in vitro cultures of Moringa peregrina (Forssk.) Fiori, *Res. Pharm. Sci.* 7:51-6 (2012).
Eilert et al., The antibiotic principle of seeds of Moringa oleifera and Moringa stenopetala, *Planta. Med.* 42:55-61 (1981).
Extended European Search Report, PCT/US2016/024924 (dated Nov. 6, 2018).
International Preliminary Report on Patentability, PCT/US2016/024924 (dated Oct. 10, 2017).
International Search Report and Written Opinion, PCT/US2016/024924 (dated Jun. 30, 2016).
Jaja-Chimedza et al., Biochemical characterization and anti-inflammatory properties of an isothiocyanate-enriched moringa (Moringa oleifera) seed extract, PLoS One. 12:e0182658 (2017).
Kim et al., A 14-day repeated dose oral toxicological evaluation of an isothiocyanate-enriched hydro-alcoholic extract from Moringa oleifera Lam. seeds in rats, *Toxicology Reports.* 5:418-26 (2018).
Mahajan et al., Inhibitory Action of Ethanolic Extract of Seeds of Moringa oleifera Lam. On Systemic and Local Anaphylaxis, *J. Immunotoxicol.* 4:287-94 (2007).
Okuda et al., Isolation and characterization of coagulant extracted from *Moringa oleifera* seed by salt solution. *Wat. Res.* 35: 405-10 (2001).
Oluduro et al., Characterization and antimicrobial activity of 4-(β-D-glucopyranosyl-1→4-α-L-rhamnopyranosyloxy)-benzyl thiocarboxamide; a novel bioactive compound from *Moringa oleifera* seed extract. *Folia Microbiol.* 55: 422-6 (2010).
Oluduro et al., Evaluation of antibacterial potential of crude extract of *Moringa oleifera* seed on orthopaedics would isolates and characterization of phenylmethanamine and benzyl isothiocyanate derivatives. *Res. J. Medicinal Plant*, 6(5): 383-94 (2012).
Rockwood et al., Potential uses of *Moringa oleifera* and an examination of antibiotic efficacy conferred by M. oleifera seed and leaf extracts using crude extraction techniques available to underserved indigenous populations. *Inter. J. Phytother. Res.* 3: 61-71 (2013).
Waterman et al., Isothiocyanate-rich Moringa oleifera extract reduces weight gain, insulin resistance, and hepatic gluconeogenesis in mice, *Mol. Nutr. Food. Res.* 59:1013-24 (2015).
Ghasi et al., Hypocholesterolemic Effects of Crude Extract of Leaf of *Moringa oleifera* Lam in High-Fat Diet Fed Wistar Rats, *Journal of Ethnopharmacology.* 69:21-25 (2000).
Author Abdulla Sahib Title of publication—Anuboga Vaithya Navaneetham Page(s) being submitted—7 (p. No. 4-10) ( Ref.p. No. of publication:31,32 ) Publication Date—(Edn: 2nd,2002) Part—10 Publisher—Thamarai Noolagam, Place of Publication—Chennai., India.†
Author Kandasamy Mudaliar. Title of publication—Aavialikkum Amuthamurai Churukkam Page(s) being submitted—5 (p. No. 11-15) ( Ref.p. No. of publication:426 ) Publication Date—( Edn: 1st. 1975.) Publisher—Palani Thandayuthapani Devasthanam publications Place of Publication—Chennai, India.†
Author Abdulla Sahib Title of publication—Anuboga Vaithya Navaneetham Page(s) being submitted—9 (p. No. 16-24) ( Ref.p.

(56) References Cited

OTHER PUBLICATIONS

No. of publication:105 ) Publication Date—(Edn: 2nd,2002) Part—10 Publisher—Thamarai Noolagam. Place of Publication—Chennai., India.†

\* cited by examiner
† cited by third party

EXTRACTS FROM PLANTS OF THE MORINGACEAE FAMILY AND METHODS OF MAKING

CROSS-REFERENCE TO RELATED APPLICATIONS

This application is a continuation-in-part of PCT/US2014/063178, filed Oct. 30, 2014, which claims the benefit of priority to U.S. Provisional Application No. 61/898,795, filed Nov. 1, 2013 and U.S. Provisional Application No. 62/032,496, filed Aug. 1, 2014, the disclosures of which are incorporated herein by reference in their entireties.

BACKGROUND OF THE INVENTION

*Moringa* (*Moringa oleifera* L.) is a fast growing tropical tree known as the "drumstick or horse radish tree." *M. oleifera* belongs to the monogenic family Moringaceae which contains only one genus and 13 species. The family is in the order Brassicales, to which broccoli and other cruciferous vegetables belong as members of Brassicaceae. *Moringa* leaves are historically used as nutritious foods and traditional medicine in Asia and Africa. *Moringa* leaves contain approximately 27% protein by dry weight, and all essential amino acids. In addition, *moringa* leaves contain high levels of vitamins, and beneficial phytoactives (Pandey et al., 2012). These include polyphenols and four unique sugar-modified aromatic glucosinolates (GLSs; Bennett et al., 2003).

Moringaceae isothiocyanates (ITCs) are formed from their glycosylated precursors, glucosinolates, via a reaction carried out by myrosinase (thioglucoside glucohydrolase). Myrosinase cleaves the thio-linked glucose in GLS, leaving the aglycone which rearranges quickly to form the active ITC. Despite well-documented health benefits of ITCs from crucifers, such as sulforaphane (SF) from broccoli and phenethylisothiocyanate from winter cress in treating inflammation and cancer, their clinical and dietary use is somewhat restricted because of their inherent chemical instability. For example SF, formed from broccoli glucoraphanin, its GLS precursor, is rapidly converted to several degradation products, mainly dimethyl disulfide and S-methyl methylthiosulfinate, making it difficult to formulate and deliver by means other than eating fresh vegetables (Franklin et al., 2013). Consuming ITCs from crucifers in their non-active, but more stable, GLS precursor form remains an option. However, GLSs undergo an uncertain and variable degree of enzymatic conversion to ITCs by host gut microbiota (Traka & Mithen, 2009) resulting in low yields and reduced or non-existent health benefits.

SUMMARY OF THE INVENTION

The present disclosure is based in part on the discovery that the enzyme necessary to convert *moringa* glucosinolates (MGLs) into *moringa* isothiocyanates (MICs) (i.e., myrosinase) can be activated by simply injuring plant material (e.g., seeds, or fresh leaves or sprouts) of a plant of the Moringaceae family, without first subjecting the plant material to harsh conditions, such as harsh temperatures and drying conditions. Once the seeds, fresh leaves or sprouts of the plant are injured, the plant material can then be dried, stored and subject to extraction at a later time to retrieve the isothiocyanates.

In one aspect, described herein is a method of activating myrosinase present in a plant of the Moringaceae family comprising injuring fresh leaves or sprouts of the plant at a temperature of less than 100° C. for a time sufficient to activate myrosinase present in the plant. In some embodiments, the injuring step is optionally performed at room temperature. In some embodiments, the injuring comprises pressing, slicing, blending, juicing, rolling, pulverizing or grinding fresh leaves or sprouts of the plant. In some embodiments, the plant of the Moringaceae family is a *M. oleifera* plant. In some embodiments, the method comprises injuring both leaves and sprouts of a plant of the Moringaceae family.

In another aspect, described herein is a method of activating myrosinase present in a plant of the Moringaceae family comprising incubating injured seeds of the plant in a solution comprising water at a temperature of less than 100° C. for a time sufficient to activate myrosinase present in the plant. In some embodiments, the seeds are injured in a solution comprising water at room temperature. In some embodiments, the injuring comprises pressing, slicing, blending, juicing, rolling, pulverizing or grinding the seeds of the plant. In some embodiments, the plant of the Moringaceae family is a *M. oleifera* plant.

In another aspect, described herein is a method of producing a plant composition comprising injuring fresh leaves or sprouts of a plant of the Moringaceae family at a temperature of less than 100° C. to produce the plant composition, wherein the plant composition comprises at least 0.1 wt % *moringa* isothiocyanates. In some embodiments, the method comprises injuring both leaves and sprouts of a plant of the Moringaceae family. In some embodiments, the injuring is optionally performed at room temperature. In some embodiments, the injuring is performed in the presence of water. In some embodiments, the injuring is performed in the absence of water.

In another aspect, described herein is a method of producing a plant composition comprising contacting injured seeds of a plant of the Moringaceae family with a solution comprising water at a temperature of less than 100° C. to produce the plant composition, wherein the plant composition comprises at least 0.1 wt % *moringa* isothiocyanates. In some embodiments, the injuring is optionally performed at room temperature.

In some embodiments, the methods of producing a plant composition as described herein optionally comprises the step of separating solid plant material (i.e., seeds, leaves or sprouts) from the plant composition. The separating step can be performed using any method known in the art including, but not limited to, filtration, sedimentation, centrifugation, evaporation, including reduced-pressure evaporation (e.g., rotavap), reduced-pressure distillation (less than 100° C.), precipitation, and adsorption.

In yet another aspect, described herein is a method of producing an extract from a plant of the Moringaceae family comprising contacting fresh injured leaves or sprouts of the plant with an extraction fluid comprising water at a temperature of less than 100° C. to produce an extraction mixture; and separating solid leaves or sprouts from the extraction mixture to produce the extract.

In yet another aspect, described herein is a method of producing an extract from a plant of the Moringaceae family comprising contacting injured seeds from the plant with an extraction fluid to produce the extract, wherein the injured seeds are incubated in a solution comprising water at a temperature of less than 100° C. for a time sufficient to activate myrosinase present in the seeds prior to the contacting step. In some embodiments, the injured seeds are incubated in a solution comprising an amount of water ranging from 1:1 (w/v) to about 1:4 (w/v). In some embodiment, the seeds are injured in a solution comprising an amount of water ranging from 1:1 (w/v) to about 1:4 (w/v). The method optionally comprises separating solid seed material from the extract.

In some embodiments, the contacting step is optionally performed at room temperature. The separating step can be performed using any method known in the art including, but not limited to, filtration, sedimentation, centrifugation, evaporation, including reduced-pressure evaporation (e.g., rotavap), reduced-pressure distillation (less than 100° C.), precipitation, and adsorption. In some embodiments, the methods further comprises injuring the seeds, leaves or sprouts by pressing, slicing, blending, juicing, rolling, pulverizing or grinding the seeds, fresh leaves or sprouts. In some embodiments, the methods optionally further comprises the step of drying the extract. Exemplary drying methods include, but are not limited to, air drying, spray drying, speed vacuum, rotoevaporation and lyophilization. In some embodiments, the method optionally comprises drying the injured fresh leaves or sprouts of the plant prior to the contacting step.

In yet another aspect, disclosed herein is a method of producing an extract from a plant of the Moringaceae family comprising injuring fresh leaves or sprouts of the plant; drying the injured fresh leaves or sprouts to produce dried injured fresh leaves or sprouts; contacting dried injured leaves or sprouts with an extraction fluid comprising water at a temperature of less than 100° C. to produce an extraction mixture; and separating solid leaves or sprouts from the extraction mixture to produce the extract.

In any of the methods described herein, the methods optionally comprise contacting both leaves and sprouts of a plant of the Moringaceae family with the extraction fluid.

In some embodiments, the extraction fluid comprises at least 95% water. In some embodiments, the solvent mixture optionally comprises fresh leaves or sprouts to extraction fluid at a 1:5 (w/v) ratio.

In other embodiments, the extraction fluid comprises 95% ethanol. In such embodiments, the contacting step comprising contacting injured seeds with an extraction fluid in an amount ranging from 1:5 (w/w) to about 1:20 (w/w).

Plant compositions and extracts produced by the methods described herein are also provided. In some embodiments, the extracts produced by the methods disclosed herein comprise at least at least 0.5% *moringa* isothiocyanates per gram of fresh injured leaves or sprouts. In some embodiments, the extracts produced by the methods disclosed herein comprise at least 1.5% *moringa* isothiocyanates per gram of fresh injured leaves or sprouts. In some embodiments, the extracts produced by the methods described herein comprise at least 1% *moringa* isothiocyanates per gram of seeds In some embodiments, the *moringa* isothiocyanates are selected from the group consisting of 4-[(α-rhamnosyloxy)benzyl]isothiocyanate (MIC-1) and 4-[(4'-O-acetyl-α-rhamnosyloxy)benzyl]isothiocyanate (MIC-4). In some embodiments, the *moringa* isothiocyanate is MIC-1.

In another aspect, the disclosure provides a method for maintaining healthy body weight in a mammalian subject in need thereof comprising administering a plant composition or extract prepared according to the methods described herein to the subject in an amount sufficient to maintain a healthy body weight in the subject. The phrase "healthy body weight" as used herein refers to a body weight that is within the normal range on the body mass index (BMI). BMI is a number calculated from a person's weight and height. A BMI of 19-24 is considered normal, while BMIs of 25-29 are defined as overweight. In some embodiments, the disclosure provides a method of promoting or maintaining a normal BMI comprising administering a plant composition or extract prepared according to the methods described herein to the subject in an amount sufficient to maintain or promote a normal BMI in the subject. In another aspect, the disclosure provides a method for promoting a healthy metabolism in a mammalian subject in need thereof comprising administering a plant composition or extract prepared according to the methods described herein to the subject in an amount sufficient to promote a healthy metabolism in the subject. In some embodiments, the subject is suffering from a metabolic disorder.

In another aspect, the disclosure provides a method for treating a mammalian subject suffering from a metabolic disorder comprising administering to the subject in need thereof a plant composition or extract produced by the methods described herein in an amount sufficient to treat the metabolic disorder. Exemplary metabolic disorders include, but are not limited to, diabetes (e.g., type I or type II diabetes), obesity, diabetes as a consequence of obesity, hyperglycemia, dyslipidemia, hypertriglyceridemia, syndrome X, insulin resistance, impaired glucose tolerance (IGT), diabetic dyslipidemia, hyperlipidemia, a cardiovascular disease, and hypertension. In some embodiments, the subject is suffering from type II diabetes. In some embodiments, the subject is suffering from obesity.

The subject may be, e.g., a human. In some embodiments, the plant composition or extract is administered to the subject over the course of, e.g., 1 year, 6 months, 3 months, 1 month, 2 weeks, 1 week, 3 days, or 1 day. In some embodiments, the subject may also be administered a second therapeutic for treating the metabolic disorder. Exemplary second therapeutics for treating the metabolic disorder include, but are not limited to, an antidiabetic agent, an antihyperuricemic agent, a lipid-lowering/lipid-modulating agent, or an anti-obesity agent, such as those described herein. In other embodiments, the second therapeutic is used for its known purpose and is selected from non-sulfonylurea secretagogues, glucagon-like peptides, exendin-4 polypeptides, PPAR agonists, dipeptidyl peptidase IV inhibitors, .alpha.-glucosidase inhibitors, immunomodulators, angiotensin converting enzyme inhibitors, adenosine A1 receptor agonists, adenosine A2 receptor agonists, aldosterone antagonists, .alpha.1 adrenoceptor antagonists, .alpha.2 adrenoceptor agonists, angiotensin receptor antagonists, antioxidants, ATPase inhibitors, atrial peptide agonists, β adrenoceptor antagonists, calcium channel agonists, calcium channel antagonists, diuretics, dopamine D1 receptor agonists, endopeptidase inhibitors, endothelin receptor antagonists, guanylate cyclase stimulants, phosphodiesterase V inhibitors, protein kinase inhibitors, Cdc2 kinase inhibitors, renin inhibitors, thromboxane synthase inhibitors, vasopeptidase inhibitors, vasopressin 1 antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholesteryl ester transfer protein antagonists, cytokine synthesis inhibitors, DNA polymerase inhibitors, dopamine D2 receptor agonists, endothelin receptor antagonists, growth hormone antagonists, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, cannabinoid receptor antagonists, cholecystokinin A agonists, corticotropin-releasing factor agonists, dopamine uptake inhibitors, G protein-coupled receptor modulators, glutamate antagonists, melanin-concentrating hormone receptor antagonists, nerve growth factor agonists, neuropeptide Y agonists, neuropeptide Y antagonists, serotonin-norepinephrine reuptake inhibitors (SNRIs), protein tyrosine phosphatase inhibitors, and serotonin 2C receptor agonists.

In any of the ranges described herein, the endpoints of the range are included in the range. Additional features and variations of the invention will be apparent to those skilled in the art from the entirety of this application and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

DETAILED DESCRIPTION

Figure 1:
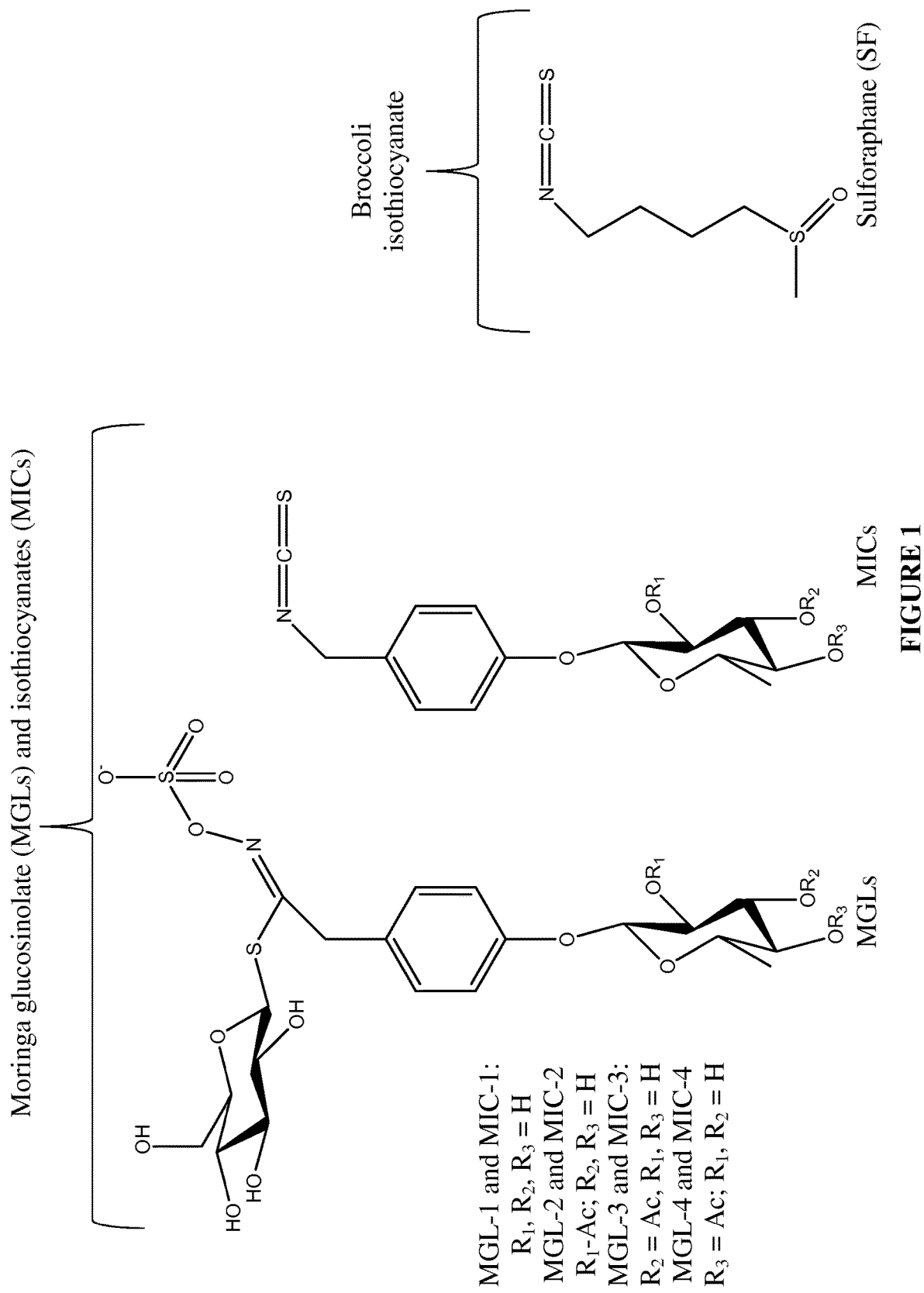
FIG. 1 provides the chemical structures of *moringa* glucosinolates (MGLs) and *moringa* isothiocyanates (MICs) from *M. oleifera* and sulforaphane (SF) from broccoli.

*Moringa* leaves contain considerable quantities of bioactive phytochemicals, including polyphenols and glucosinolates. While not biologically active, glucosinolates can be converted to isothiocyanates by the naturally occurring enzyme, myrosinase. Isothiocyanates isolated from a plant of the Moringaceae family are structurally related to sulforaphane found in broccoli, but contain an unusual, if not a unique substitute rhamnose moiety which confers greatly enhanced stability and bioavailability compared to sulforaphane.

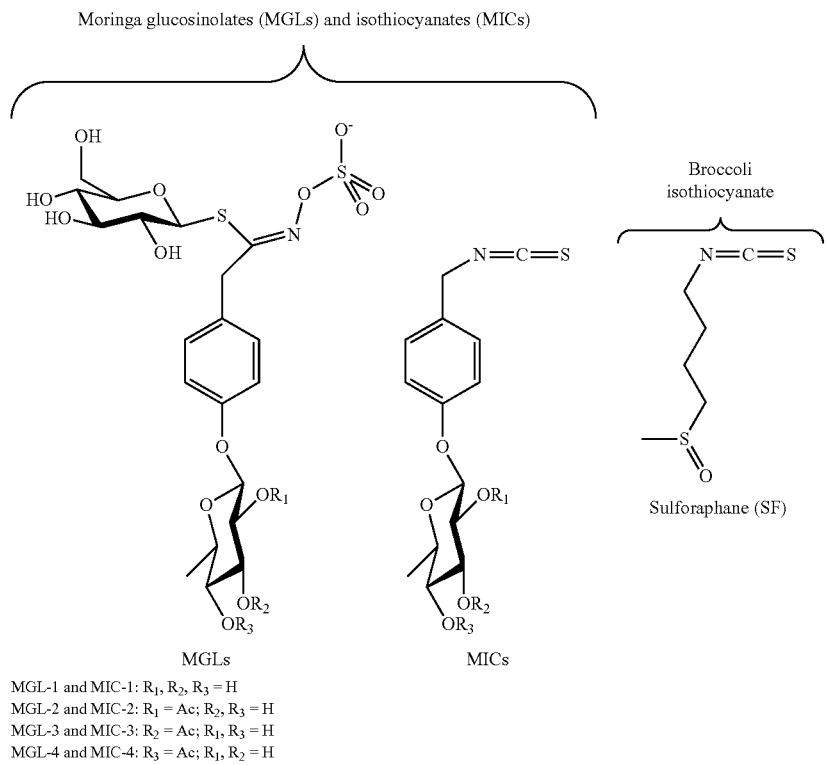

MGL-1 and MIC-1: $R_1, R_2, R_3 = H$
MGL-2 and MIC-2: $R_1 = Ac; R_2, R_3 = H$
MGL-3 and MIC-3: $R_2 = Ac; R_1, R_3 = H$
MGL-4 and MIC-4: $R_3 = Ac; R_1, R_2 = H$ As shown above, *moringa* glucosinolates (MGLs) contain an additional sugar moiety in the aglycone/isothiocyanate portion of the molecule. These MGLs can be converted in situ to four bioactive and relatively stable *moringa* isothiocyanates (MICs), referred to as MIC-1 through MIC-4. MIC-1 (4-[(α-rhamnosyloxy)benzyl]isothiocyanate) and MIC-4 (4-[(4'-O-acetyl-α-rhamnosyloxy)benzyl]isothiocyanate) are the most abundant MICs, formed from MGL-1 and MGL-4. MICs are solid and relatively stable compounds at room temperature, in contrast to volatile isothiocyanates from crucifers that are mostly viscous liquids. The retained rhamnose sugar moiety found in MICs is extremely unique in nature and likely responsible for the high stability and solid appearance (Brunelli et al., 2010).

The present disclosure is based in part on the discovery that the enzyme necessary to convert *moringa* glucosinolates (MGLs) into *moringa* isothiocyanates (MICs) (i.e., myrosinase) can be activated by simply injuring plant material (e.g., seeds, fresh leaves or sprouts) of a plant of the Moringaceae family, without first subjecting the plant material to harsh conditions, such as harsh temperatures and harsh drying conditions. This simple method can be used to effectively convert MGLs into MICs to produce a shelf-stable *moringa* plant extract containing more than 1.0% MICs. Harsh procedures used for the manufacture of *moringa* leaf powder, such as high temperatures or outdoor drying prior to injuring the plant material, usually lead to almost complete degradation of MGLs and MICs. As demonstrated in Example 2, analysis of several samples of *moringa* leaf powder from multiple commercial vendors confirmed the absence, or significant reduction, in levels of these desirable compounds. Similarly, the inventors have discovered that the use of a harsh solvent, such as 95% ethanol, in an extraction method prior to injuring seed material in a solution comprising water (or incubating injured seed material in a solution comprising water) inhibits formation of MICs. As demonstrated in Example 8, incubating injured seeds in a solution comprising water, or injuring seeds in a solution comprising water produced optimal conditions for activating myrosinase and forming MICs. Adding solvent (e.g., ethanol) to the injured seeds before water progressively inhibited formation of MICs. No detectable MICs were formed when 95% ethanol was directly added to the injured seeds or when the seeds were injured in 95% ethanol.

Thus, in one aspect, disclosed herein is a method of activating myrosinase present in a plant of the Moringaceae family comprising injuring fresh leaves or sprouts of the plant at a temperature of less than 100° C. for a time sufficient to activate myrosinase present in the plant. In some embodiments, the plant of the Moringaceae family is a *M. oleifera* plant.

In another aspect, disclosed herein is a method of activating myrosinase present in a plant of the Moringaceae family comprising contacting injured seeds of the plant with a solution comprising water for a time sufficient to activate myrosinase present in the plant. In some embodiments, the contacting occurs at a temperature of less than 100° C.

The phrase "solution comprising water" as used herein refers to a solution comprising at least 50% water. In some embodiments, at least 55%, or at least 60%, or at least 65%, or at least 70%, or at least 75%, or at least 80%, or at least 90%, or at least 95%, or at least 99% or more of the solution comprises water.

In some embodiments, the methods disclosed herein utilize fresh leaves or sprouts of a plant from the Moringaceae family. The term "fresh leaves or sprouts" of a plant of the Moringaceae family as used herein refers to leaves or sprouts of the plant that have not been dried or that have not been subjected to mechanical or chemical processing prior to their use in the methods disclosed herein.

In some embodiments, the methods disclosed herein utilize seeds of a plant from the Moringaceae family.

The term "injuring" as used herein refers to a method of processing seeds or the fresh leaves or sprouts of the plant such that the myrosinase present in the seeds, fresh leaves or sprouts of the plant is preserved and activated. In some embodiments, the "injuring" comprises pressing, slicing, blending, juicing, rolling, pulverizing or grinding the seeds, fresh leaves or sprouts of the plant.

Because the processing of *moringa* plant material at high temperatures is associated with the degradation of myrosinase in the plant material, the methods described herein are performed at a temperature of less than 100° C., optionally at a temperature ranging from 18° C. to 100° C. In some embodiments, the methods described herein are performed at a temperature of less than 90° C., or less than 85° C., or less than 80° C., or less than 75° C., or less than 70° C., or less than 65° C., or less than 60° C., or less than 55° C., or less than 50° C., or less than 45° C., or less than 40° C., or less than 35° C., or less than 30° C., or less than 25° C., or less than 20° C. In some embodiments, the methods described herein are performed at a temperature of about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., or about 99° C. In some embodiments, the methods described herein are performed at room temperature. The term "room temperature" as used herein refers to a temperature generally ranging from 18° C. to 25° C.

Also described herein is a method of producing a plant composition comprising blending fresh leaves or sprouts of a plant of the Moringaceae family at a temperature of less than 100° C. to produce the plant composition, wherein the plant composition comprises at least 0.05 wt % *moringa* isothiocyanates (MICs). A plant composition can also be prepared by a method comprising contacting injured seeds of a plant of a Moringaceae family with a solution comprising water at a temperature of less than 100° C. to produce the plant composition, wherein the plant composition comprises at least 1 wt % MICs. In some embodiments, the plant of the Moringaceae family is a *M. oleifera* plant. The term "plant composition" as used herein refers to a composition obtainable from a plant of the Moringaceae family without the use of an extraction fluid, as that term is defined below. In some embodiments, the plant composition comprises about 0.05 wt % MICs or about 0.1 wt % MICs or about 0.2 wt % MICs or about 0.3 wt % MICs. In some embodiments, the method of producing the plant composition is performed at a temperature of less than 100° C., optionally at a temperature ranging from 18° C. to 100° C. In some embodiments, the method is performed at a temperature of less than 90° C., or less than 85° C., or less than 80° C., or less than 75° C., or less than 70° C., or less than 65° C., or less than 60° C., or less than 55° C., or less than 50° C., or less than 45° C., or less than 40° C., or less than 35° C., or less than 30° C., or less than 25° C., or less than 20° C. In some embodiments, the method is performed at a temperature of about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., or about 99° C. In some embodiments, the method is performed at room temperature, as that term is defined herein.

The method optionally further comprises separating solid plant material (e.g., seeds, leaves or sprouts) from the plant composition. Exemplary methods of separation include, but are not limited to, filtration, sedimentation, centrifugation, evaporation, including reduced-pressure evaporation (e.g., rotavap), reduced-pressure distillation (less than 100° C.), precipitation, and adsorption. In some embodiments, the resulting plant composition is dried, but the drying is performed post-injury, permitting endogenous myrosinase an opportunity to at least partially convert MGLs to MICs. Exemplary methods of drying the plant composition include, but are not limited to, air drying, speed vacuum, rotoevaporation and lyophilization.

Also described herein are methods of producing an extract from a plant of the Moringaceae family. In some embodiments, the plant of the Moringaceae family is a *M. oleifera* plant. In some embodiments, the method comprises contacting fresh injured leaves or sprouts of the plant with an extraction fluid comprising water at a temperature of less than 100° C. to produce an extraction mixture; and separating solid leaves and/or sprouts from the extraction mixture to produce the extract.

Also described herein are methods of producing an extract from seeds of a plant Moringaceae family. In some embodiments, the plant of the Moringaceae family is a *M. oleifera* plant. In some embodiments, the method comprises contacting injured seeds of the plant with an extraction fluid to produce the extract, wherein the injured seeds are incubated in a solution comprising water at a temperature of less than 100° C. for a time sufficient to activate myrosinase present in the seeds prior to the contacting step. In some embodiments, the injured seeds are incubated in a solution comprising an amount of water ranging from 1:1 (w/v) to about 1:4 (w/v). In some embodiment, the seeds are injured in a solution comprising an amount of water ranging from 1:1 (w/v) to about 1:4 (w/v).

The injured seeds are incubated in a solution comprising water (or injured in a solution comprising water) at a temperature of less than 100° C., optionally at a temperature ranging from 18° C. to 100° C. In some embodiments, the method is performed at a temperature of less than 90° C., or less than 85° C., or less than 80° C., or less than 75° C., or less than 70° C., or less than 65° C., or less than 60° C., or less than 55° C., or less than 50° C., or less than 45° C., or less than 40° C., or less than 35° C., or less than 30° C., or less than 25° C., or less than 20° C. In some embodiments, the method is performed at a temperature of about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., or about 99° C. In some embodiments, the method is performed at room temperature, as that term is defined herein.

In some embodiments, the injured seeds are incubated with a solution comprising a volume of water at an exemplary ratio of 1:1 (i.e., grams of seeds used to volume of water (mL)). In other embodiments, the injured seeds are incubated with a solution comprising a volume of water at an exemplary ratio of 1:2, or 1:3, or 1:4, or 1:5. In some embodiments, the injured seeds are incubated with a solution comprising a volume of water at a ratio of 1:3.

In some embodiments, the method of producing the extract is performed at a temperature of less than 100° C., optionally at a temperature ranging from 18° C. to 100° C. In some embodiments, the method is performed at a temperature of less than 90° C., or less than 85° C., or less than 80° C., or less than 75° C., or less than 70° C., or less than 65° C., or less than 60° C., or less than 55° C., or less than 50° C., or less than 45° C., or less than 40° C., or less than 35° C., or less than 30° C., or less than 25° C., or less than 20° C. In some embodiments, the method is performed at a temperature of about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., or about 99° C. In some embodiments, the method is performed at room temperature, as that term is defined herein.

Solid plant material (e.g., seeds, leaves and/or sprouts) can be separated from the extraction mixture by any method known in the art including, but not limited to, filtration, sedimentation, centrifugation, evaporation, including reduced-pressure evaporation (e.g., rotavap), reduced-pressure distillation (less than 100° C.), precipitation, and adsorption. In some embodiments, the separating step comprises filtering the extraction mixture to produce the extract. Any filter material and apparatus known in the art are contemplated for use in filtering the extraction mixture.

In other embodiments, the method of producing an extract from a plant of the Moringaceae family comprises injuring fresh leaves or sprouts of the plant, drying the injured leaves or sprouts, contacting dried injured leaves or sprouts with an extraction fluid comprising water at a temperature of less than 100° C. to produce an extraction mixture, and separating solid leaves and/or sprouts from the extraction mixture to produce the extract.

The injured fresh leaves or sprouts of the plant are preferably dried at a temperature that permits endogenous myrosinase an opportunity to at least partially convert MGLs to MICs. In some embodiments, the injured fresh leaves or sprouts are dried using a method including, but not limited to, heat drying, air drying or microwaves. In some embodiments, the injured fresh leaves or sprouts are dried at a temperature of less than 100° C., optionally at a temperature ranging from 18° C. to 100° C. In some embodiments, the injured fresh leaves or sprouts are dried at a temperature of less than 90° C., or less than 85° C., or less than 80° C., or less than 75° C., or less than 70° C., or less than 65° C., or less than 60° C., or less than 55° C., or less than 50° C., or less than 45° C., or less than 40° C., or less than 35° C., or less than 30° C., or less than 25° C., or less than 20° C. In some embodiments, the injured fresh leaves or sprouts are dried at a temperature of about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., or about 99° C. In some embodiments, the injured fresh leaves or sprouts are dried at about 37° C. In some embodiments, the injured fresh leaves or sprouts are dried at room temperature, as that term is defined herein.

The term "extract from a plant of the Moringaceae family" as used herein means a substance or composition obtained from injured seeds and/or injured fresh leaves or sprouts of a plant of the Moringaceae family (or obtained from dried, injured fresh leaves or sprouts of a plant of the Moringaceae family, wherein the fresh leaves or sprouts were injured before being dried) through the use of an extraction fluid. Chemical and/or physical action, as would be understood in the art, may be required to obtain the substance or composition from the seeds, fresh leaves or sprouts of the plant (or obtained from dried, injured fresh leaves or sprouts of a plant of the Moringaceae family).

An "extraction fluid" for use in extraction methods includes water and well-known organic solvents such as, but not limited to, alcohols, alkanes, halocarbons, ethers, aromatic solvents, ketones, aqueous solvents, esters, and supercritical fluids. In some embodiments, ethanol is used to practice an extraction method described herein. In some embodiments, the extraction fluid used to practice the extraction methods described herein include, but are not limited to, 40% ethanol, 50% ethanol, 70% ethanol and 95% ethanol. Like water, a benefit of incorporating an ethanolic solvent in extraction method is that an ethanolic solvent is compatible with an ingestible product, and therefore is suitable for incorporation of the extract into a pill, capsule, tablet, or other ingestible form known in the art. In some embodiments, the extraction fluid comprises at least 90%, or at least 91%, or at least 92%, or at least 93%, or at least 94%, or at least 95%, or at least 96%, or at least 97%, or at least 98%, or at least 99% water. In some embodiments, the extraction fluid comprises less than 10%, or less than 9%, or less than 8%, or less than 7%, or less than 6%, or less than 5%, or less than 4%, or less than 3%, or less than 2%, or less than 1% of an organic solvent other than water. Exemplary organic solvents other than water include, but are not limited to, straight and branched chain alkanes, alcohols, ethers, esters, aldehydes, ketones, and hydrocarbons of C1 to C10, e.g., ethanol, methanol, n-butanol, n-propanol and isopropanol. In some embodiments, the extraction fluid comprises 95% ethanol.

In some embodiments, the injured fresh leaves or sprouts of the plant are contacted with a volume of extraction fluid at an exemplary ratio of 1:1 (i.e., grams of fresh plant material used to volume of extraction fluid (mL)). In other embodiments, the injured fresh leaves or sprouts of the plant are contacted with a volume of extraction fluid at an exemplary ratio of 1:2, or 1:3, or 1:4, or 1:5, or 1:6, or 1:7, or 1:8, or 1:9 or 1:10. In some embodiments, the injured fresh leaves or sprouts of the plant are contacted with a volume of extraction fluid at a ratio of 1:5.

In some embodiments, the injured seeds (that are either incubated in a solution comprising water after injury, or are injured in a solution comprising water prior to the contacting step) are contacted with a volume of extraction fluid at an exemplary ratio of 1:5 (e.g., grams of injured seed material to volume of extraction fluid (mL). In other embodiments, the injured seeds are contacted with a volume of extraction fluid at an exemplary ratio of 1:6, or 1:7, or 1:8, or 1:9, or 1:10, or 1:11, or 1:12, or 1:13, or 1:14 or 1:15, or 1:16, or 1:17, or 1:18, or 1:19, or 1:20. In some embodiments, the injured seeds are contacted with a volume of extraction fluid at a ratio of 1:5.

The extract produced by the extraction methods described herein comprises a high concentration of *moringa* isothiocyanates (MICs) compared to extracts produced using a dried *moringa* leaf powder as the starting material. In some embodiments, the extract comprises at least 0.5% MICs per gram of plant material (e.g., seeds, leaves or sprouts) used in the extraction method. In some embodiments, the extract comprises at least 0.6%, or at least 0.7%, or at least 0.8%, or at least 0.9%, or at least 1%, or at least 1.1%, or at least 1.2%, or at least 1.3%, or at least 1.4%, or at least 1.5%, or at least 1.6%, or at least 1.7%, or at least 1.8%, or at least 1.9%, or at least 2%, or at least 5%, or at least 10% or more MICs per gram of plant material (e.g., seeds, leaves or sprouts) used in the extraction method. In some embodiments, the extract comprises about 1% MICs per gram of plant material (e.g., seeds, leaves or sprouts) used in the extraction method. In some embodiments, the extract comprises about 1.5% MICs per gram of plant material (e.g., seeds, leaves or sprouts) used in the extraction method.

The MICs present in an extract produced by the methods disclosed herein demonstrate greater stability than other isothiocyanates, such as sulforaphane. For example, in some embodiments, an extract produced by the methods disclosed herein comprise a MIC that demonstrated less than 50% degradation when the extract was stored at 37° C. for about 30 days compared to the MIC present in the extract at day 0. In some embodiments, a MIC in the extract degrades less than 50%, less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2% or less than 1% when the extract is stored at 37° C. for about 30 days. In some embodiments, MIC-4 in the extract produced by the methods disclosed herein degrades less than 20% when the extract is stored at 37° C. for about 30 days compared to the amount of MIC-4 present in the extract at day 0.

Extracts obtained from plants of the Moringaceae family contain other beneficial phytochemicals, such as polyphenols, flavonols, carotenoids, and ascorbic acid. Polyphenols found in plants of the Moringaceae family include, but are not limited to, to 5-caffeoylquinic acid (5-CQA), 3-caffeoylquinic acid (3-CQA), quercetin 3-O-rutinoside, quercetin 3-O-glucoside, kaempferol 3-O-rutinoside, quercetin 3-O-(6''-malonylglucoside), kaempferol 3-O-glucoside, quercetin 3-O—(X''-malonylglucoside),isorhamnetin 3-O-glucoside, quercetin 3-O—(X''-acetylglucoside, quercetin 3-O—(Y''-malonylglucoside), kaempferol 3-O-(6''-malonylglucoside), isorhamnetin 3-O-(6''-malonylglucoside), kaempferol 3-O—(X''-malonylglucoside), kaempferol 3-O—(X''-acetylglucoside), quercetin aglycone, kaempferol aglycone, isorhamnetin aglycone. The most abundant being 5-caffeoylquinic acid (5-CQA) known as chlorogenic acid, quercetin-3-O-rutinoside known as rutin, quercetin 3-O-glucoside and quercetin 3-O-(6''-malonylglucoside). In some embodiments, an extract produced by the methods described herein comprises (in addition to a high concentration of MICs) at least 1% total polyphenol content per gram of plant material used in the extraction method. In some embodiments, an extract produced by the methods described herein comprises at least 1%, or at least 2%, or at least 3%, or at least 4%, or at least 5%, or at least 6%, or at least 7%, or at least 8%, or at least 9%, or at least 10% total polyphenol content per gram of plant material. In some embodiments, an extract produced by the methods described herein comprises a total polyphenol content ranging from 2-5%, or 1-3%, or 2-4%, or 1-5%, or 3-5%, or 3-7% or 4-8% or 5-10% per gram of plant material.

Use of the Plant Compositions or Extracts

In some embodiments, a plant composition or extract produced by the methods described herein is incorporated into consumer products. Consumer products are products available for purchase and/or use by individual consumers and include food products (including, but not limited to, enriched food products (see below), dietary supplements (see below) and medical foods (see below)), cosmetic products and other personal care products.

In some embodiments the plant composition or extract produced by the methods described herein is incorporated into a food product to produce an enriched food product. The term "food product" as used herein refers to any substance containing nutrients that can be ingested by an organism to produce energy, promote health and wellness, stimulate growth, and maintain life. In some embodiments, the plant composition or extract produced by the methods described herein is used in the preparation of enriched food products comprising high amounts of MICs. The term "enriched food product" as used herein refers to a food product that has been modified to include the plant composition or extract produced by the methods described herein described herein, which provides a benefit such as a health/wellness-promoting and/or disease-preventing/mitigating/treating property beyond the basic function of supplying nutrients.

The plant composition or extract produced by the methods described herein can be incorporated into any food product. Exemplary food products include, but are not limited to, baked goods (cakes, cookies, crackers, breads, scones and muffins), dairy-type products (including, but not limited to, cheese, yogurt, custards, rice pudding, mousses, ice cream, frozen yogurt, frozen custard), desserts (including, but not limited to, sherbet, sorbet, water-ices, granitas and frozen fruit purees), spreads/margarines, pasta products and other cereal products, meal replacement products, nutrition bars, trail mix, granola, beverages (including, but not limited to, smoothies, water or dairy beverages, and soy-based beverages), and breakfast-type cereal products such as oatmeal. For beverages, the plant composition or extract (or MICs isolated from the plant composition or extract) may be in solution, suspended, emulsified or present as a solid.

In one embodiment, the enriched food product is a meal replacement product. The term "meal replacement product" as used herein refers to an enriched food product that is intended to be eaten in place of a normal meal. Nutrition bars and beverages that are intended to constitute a meal replacement are types of meal replacement products. The term also includes products which are eaten as part of a meal replacement weight loss or weight control plan, for example snack products which are not intended to replace a whole meal by themselves, but which may be used with other such products to replace a meal or which are otherwise intended to be used in the plan. These latter products typically have a calorie content in the range of from 50-200 kilocalories per serving.

In another embodiment, the food product is a dietary supplement. The term "dietary supplement" as used herein refers to a substance taken by mouth that contains a "dietary ingredient" intended to supplement the diet. The term "dietary ingredient" includes, but is not limited to, the MICs as disclosed herein, as well as vitamins, minerals, herbs or other botanicals, amino acids, and substances such as enzymes, organ tissues, glandulars, and metabolites.

In yet another embodiment, the food product is a medical food. The term "medical food" as used herein means a food which is formulated to be consumed or administered entirely under the supervision of a physician and which is intended for the specific dietary management of a disease or condition for which distinctive nutritional requirements, based on recognized scientific principles, are established by medical evaluation.

In some embodiments, the plant composition or extract produced by the methods described herein (or MICs isolated from the plant composition of extract) are useful as cosmeceuticals. The term "cosmeceutical" as used herein means an ingredient for a cosmetic, body care or hair care personal product having a positive effect on the physical condition of the body (e.g., the skin, the nails, or hair).

Compositions suitable for personal care products generally are formulated as, e.g., shampoos, conditioners, shower gels, liquid hand cleansers, facial cleansers, moisturizers, lotions, skin lotions and creams (such as eye creams and lip creams), facial skin cosmetics (such as blusher and highlighter), eye cosmetics (such as eye shadow, eye brow color, and eye liner), lip cosmetics (such as lip rouge), foundation, concealer, wrinkle-smoothing serums or creams, mascaras, skin facial masks, sunscreens, scalp hair-styling aids, facial hair-styling aids, emulsions, oils, mousses, ointments, milks, pomades, solutions, sprays, aerosols, powders, foams, gels (such as skin gels, eye gels, and lip gels), or other skin or hair products known in the art.

Additional Uses

The data provided herein demonstrate that serum levels of insulin, leptin, resistin, triglycerides and cholesterol (all of which are associated with metabolic disorders and healthy body weight maintenance) were reduced in animals receiving a *moringa* extract produced by the methods described herein. Thus, the disclosure also provides a method for maintaining healthy body weight in a mammalian subject in need thereof comprising administering a plant composition or extract prepared according to the methods described herein to the subject in an amount sufficient to maintain a healthy body weight in the subject. The phrase "healthy body weight" as used herein refers to a body weight that is within the normal range on the body mass index (BMI). BMI is a number calculated from a person's weight and height. A BMI of 19-24 is considered normal, while BMIs of 25-29 are defined as overweight. In some embodiments, the disclosure provides a method of promoting or maintaining a normal BMI comprising administering a plant composition or extract prepared according to the methods described herein to the subject in an amount sufficient to maintain or promote a normal BMI in the subject.

In another aspect, the disclosure provides a method for promoting a healthy metabolism in a mammalian subject in need thereof comprising administering a plant composition or extract prepared according to the methods described herein to the subject in an amount sufficient to promote a healthy metabolism in the subject. In some embodiments, the subject is suffering from a metabolic disorder.

In another aspect, the disclosure provides a method for treating a mammalian subject suffering from a metabolic disorder comprising administering to the subject in need thereof a plant composition or extract produced by the methods described herein in an amount sufficient to treat the metabolic disorder. In some embodiments, the subject is suffering from type II diabetes. In some embodiments, the subject is suffering from obesity.

The term "metabolic disorder" is used broadly herein to refer to the conditions, diseases, and disorders associated with insulin and/or glucose dysregulation. Such disorders include those resulting from an alteration in glucose homeostasis resulting, for example, in hyperglycemia. In some embodiments, an alteration in glucose levels is an increase in glucose levels by at least 5%, 10%, 20%, 30%, 40%, 50%, 60%, 70%, 80%, 90%, or even 100% relative to such levels in a healthy individual. Metabolic disorders include, but are not limited to, obesity and diabetes (e.g., diabetes type I, diabetes type II, MODY, and gestational diabetes), satiety, endocrine deficiencies of aging, diabetes as a consequence of obesity, hyperglycemia, dyslipidemia, hypertriglyceridemia, syndrome X (metabolic syndrome), insulin resistance, impaired glucose tolerance (IGT), diabetic dyslipidemia, hyperlipidemia, a cardiovascular disease, and hypertension. Metabolic disorders are also described in Kinzig et al., J. Neurosci. 23:6163-6170, 2003, which is hereby incorporated by reference.

By "treating" is meant ameliorating at least one symptom of a condition or disease in a subject having the condition or disease (e.g., a subject diagnosed with a metabolic disorder), as compared with an equivalent untreated control. Such reduction in the symptom (e.g., a reduction in blood glucose levels or weight) is at least 5%, 10%, 20%, 40%, 50%, 60%, 80%, 90%, 95%, or 100%, as measured by any standard technique.

In some embodiments, a desired outcome of treatment is the ability to reduce glucose levels in the subject. The phrase "reducing glucose levels" refers to reducing the level of glucose in a blood sample from the subject by at least 10%, 20%, 30%, 40%, 50%, 60%, 70%, 80%, 90%, 95%, or 100% relative to an untreated control. In some embodiments, glucose levels are reduced to normoglycemic levels, i.e., levels between 150 to 60 mg/dl, between 140 to 70 mg/dl, between 130 to 70 mg/dl, between 125 to 80 mg/dl, or between 120 to 80 mg/dl.

In some embodiments, a desired outcome of treatment is the ability to maintain a healthy body weight. The phrase "healthy body weight" as used herein refers to a body weight that is within the normal range on the body mass index (BMI). BMI is a number calculated from a person's weight and height. A BMI of 19-24 is considered normal, while BMIs of 25-29 are defined as overweight. In some embodiments, the disclosure provides a method of promoting or maintaining a normal BMI comprising administering a plant composition or extract prepared according to the methods described herein to the subject in an amount sufficient to maintain or promote a normal BMI in the subject.

Formulations and Dose Regimens

The disclosure contemplates compositions comprising a plant composition or extract produced by the methods described herein (or MICs isolated from such plant compositions and/or extracts) that are, in some embodiments, tabletted, encapsulated or otherwise formulated for oral administration. The compositions may be provided as pharmaceutical compositions, nutraceutical compositions (e.g., a dietary supplement), or as a food or beverage additive, as defined by the U.S. Food and Drug Administration. The dosage form for the above compositions is not particularly restricted. For example, liquid solutions, suspensions, emulsions, tablets, pills, capsules, sustained-release formulations, powders, suppositories, liposomes, microparticles, microcapsules, sterile isotonic aqueous buffer solutions, and the like are all contemplated as suitable dosage forms.

The compositions typically include one or more suitable diluents, fillers, salts, disintegrants, binders, lubricants, glidants, wetting agents, controlled release matrices, colorings, flavoring, carriers, excipients, buffers, stabilizers, solubilizers, commercial adjuvants, and/or other additives known in the art.

Any pharmaceutically acceptable (i.e., sterile and acceptably non-toxic as known in the art) liquid, semisolid, or solid diluent that serves as a pharmaceutical vehicle, excipient, or medium can be used. Exemplary diluents include, but are not limited to, polyoxyethylene sorbitan monolaurate, magnesium stearate, calcium phosphate, mineral oil, cocoa butter, and oil of theobroma, methyl- and propylhydroxybenzoate, talc, alginates, carbohydrates, especially mannitol, α-lactose, anhydrous lactose, cellulose, sucrose, dextrose, sorbitol, modified dextrans, gum acacia, and starch. Such compositions may influence the physical state, stability, rate of in vivo release, and rate of in vivo clearance of the functional compounds that are compatible with the disclosed methods and extracts comprising relatively stabilized MICs.

Pharmaceutically acceptable fillers can include, for example, lactose, microcrystalline cellulose, dicalcium phosphate, tricalcium phosphate, calcium sulfate, dextrose, mannitol, and/or sucrose. Salts, including calcium triphosphate, magnesium carbonate, and sodium chloride, may also be used as fillers in the pharmaceutical compositions.

Binders may be used to hold together the composition containing the enriched substance to form a hard tablet. Exemplary binders include materials from organic products such as acacia, tragacanth, starch and gelatin. Other suitable binders include methyl cellulose (MC), ethyl cellulose (EC) and carboxymethyl cellulose (CMC).

In some embodiments, the composition further comprises a bioavailability enhancer, which acts to increase the absorption of the MICs by the body. Bioavailability enhancers can be natural or synthetic compounds. In one embodiment, the enriched food product comprising the enriched solid further comprises one or more bioavailability enhancers in order to enhance the bioavailability of the bioactive natural product(s).

Natural bioavailability enhancers include ginger, a caraway extract, a pepper extract and chitosan. The active compounds in ginger include 6-gingerol and/or 6-shogoal. Caraway oil can also be used as a bioavailability enhancer (U.S. Patent Application Publication No. 2003/022838). Piperine is a compound derived from pepper (*Piper nigrum* or *Piper longum*) that acts as a bioavailability enhancer (U.S. Pat. No. 5,744,161). Piperine is available commercially under the brand name Bioperine® (Sabinsa Corp., Piscataway, N.J.). In some embodiments, the natural bioavailability enhancers is present in an amount of from about 0.02% to about 0.6% by weight based on the total weight of enriched food product.

Examples of suitable synthetic bioavailability enhancers include, but are not limited to, Gelucire®, Labrafil® and Labrasol®, Lauroglycol®, Pleurol Oleique® (Gattefosse Corp., Paramus, N.J.) and Capmul® (Abitec Corp., Columbus, Ohio).

The amount and administration regimen of the composition is based on various factors relevant to the purpose of administration, for example human or animal age, sex, body weight, hormone levels, or other nutritional need of the human or animal. In some embodiments, the composition is administered to an animal in an amount from about 0.001 mg/kg body weight to about 10 g/kg body weight. In some embodiments, the composition is administered to an animal in an amount of about 0.005 mg/kg body weight. In some embodiments, the composition is administered to an animal in an amount of about 0.01 mg/kg body weight, or about 0.05 mg/kg body weight, or about 0.1 mg/kg body weight, or about 1 mg/kg body weight, or about 10 mg/kg body weight, or about 100 mg/kg body weight, or about 250 mg/kg body weight, or about 500 mg/kg body weight, or about 1 g/kg per body weight, or about 2.5 g/kg body weight, or about 5 g/kg body weight, or about 7.5 g/kg body weight, or about 10 g/kg body weight.

A typical regimen may comprise multiple doses of the composition. In one embodiment, the composition is administered once per day and may be administered to an individual at any time. In some embodiments, the composition is administered concurrently, prior to, or at the consumption of a meal. The composition is administered on any periodic schedule suitable for the desired or needed effect, or on an as-needed basis.

It will be appreciated that the plant composition and extract produced by the methods described herein is useful in the fields of human medicine and veterinary medicine to provide high levels of MICs to a subject in need thereof. Thus, the subject or individual to be treated may be a mammal, such as a human. For veterinary purposes, subjects include, for example, farm animals such as cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

EXAMPLES

The following Examples are provided to describe the invention in greater detail, and are intended to illustrate, not to limit, the appended claims. Example 1 provides the materials and methods for the experiments performed in Example 2. Example 2 describes the optimization of the extraction method. Example 3 demonstrates that the *moringa* extracts prepared as described in Example 2 have anti-inflammatory activity. Example 4 provides additional parameters for the preparation of *moringa* plant compositions and extracts. Example 5 provide an alternative method for the preparation of a *moringa* extract. Example 6 provides the materials and methods for the experiments performed in Example 7. Example 7 demonstrates that the *moringa* extracts prepared as described in Example 2 reduced body weight and fat accumulation in mice. Example 8 provides materials and methods for the preparation of *moringa* plant compositions and extracts from seeds of a *M. oleifera* plant.

Example 1—Materials and Methods

Plant Material and Sample Preparation. Fresh leaves and seeds from *M. oleifera* (Indian PKM-1 variety) were shipped overnight from Moringa Farms, CA. The leaves were extracted using the methods disclosed herein on the day of arrival to produce a *moringa* extract. Moringa seeds were cultivated at the Rutgers University greenhouse until the plants flowered. A voucher specimen (CW1) was prepared and deposited at the Chrysler Herbarium of Rutgers University (CHRB).

Fresh *M. oleifera* leaves were blended (Vitamix 5200 Blender, Cleveland, Ohio) thoroughly with room temperature Millipore water in a ratio of 1 g of leaves to 5 mL of water (1:5) for *moringa* extract preparation used in stability tests, all biological assays and batch reproducibility assessment. Micro preparation of *moringa* extract for temperature/dilution optimization was performed by grinding fresh leaves in a coffee grinder (Krups, Millville, N.J.) and then placing them in water. The leaf extracts (either prepared with the blender or coffee grinder) were placed on a shaker for 30 min at room temperature. In temperature experiments, the extracts were placed in water baths at designated temperatures for 30 min. Following incubation, the extracts were filtered through Miracloth (Calibiochem, Billerica, Mass.) and centrifuged for 10 min at 3200 g and 4° C. The supernatant, which appeared as a brown clear tea was decanted and lyophilized to produce *moringa* extract. In some cases, particularly with larger batches, centrifugation was repeated in order to clear all solid materials from the supernatant.

Compound Extraction and Isolation.

MIC-1 and MIC-4 were isolated from fresh *moringa* leaves using a modified approach to previously published methods (Cheenpracha et al., 2010). Briefly, MICs were initially extracted from ground leaves in methanol (MeOH). The methanolic extract was dried down and partitioned in $H_2O$ and hexanes (1:1 v/v). An equal volume of ethyl acetate (EtOAc) was then added to the $H_2O$ fraction. The EtOAc fraction was dried down and resuspended in acetonitrile (CAN): $H_2O$ (1:1), sonicated briefly, and filtered through a 0.45 μm filter prior to preparative high-performance liquid chromatography (HPLC).

Replicate HPLC injections of 100 μL of the EtOAc fraction (200 mg/mL) were eluted with $ACN/H_2O$/trifluoroacetic acid (TFA) (50:50:0.05) to yield MIC-1 (retention time (Rt)=8.2 min) and MIC-4 (Rt=17.5 min). Reverse-phase HPLC was carried out on a Waters System consisting of a four-channel Waters 616 pump with semi-preparative pump heads operated on a Waters 600 Controller; Waters 490E Programmable Multiwavelength Detector set to monitor at 222 nm; and a Waters 717 Plus Autosampler. A Phenomenex semi-preparative Synergi Hydro column (4 μM, 250×20 mm) was run with a flow rate of 10 mL/min.

Compound Quantification.

The chemical purity of isolated MICs was confirmed by liquid chromatography mass spectrometry (LCMS) and $^1H$ NMR. The UV peak area of LCMS injections of MIC-1 and MIC-4 (>98% purity) at 3 concentrations (3×) were averaged and used to generate standard curves to quantify MIC content in *moringa* extract preparations. One μL injections (3×) of MIC-1 at 20, 100, and 200 ng/μL dissolved in ACN: $H_2O$ (1:1) generated a standard curve (y=123x−0.098, R2=1) and MIC-4 at 10, 50, and 100 ng/μL generated a standard curve (y=104.32x−0.098, R2>0.99).

LCMS analysis was performed using the Dionex® UltiMate 3000 RSLC ultra-high-pressure liquid chromatography system, consisting of a workstation with Dionex®'s Chromeleon v. 6.8 software package, solvent rack/degasser SRD-3400, pulseless chromatography pump HPG-3400RS, autosampler WPS-3000RS, column compartment TCC-3000RS, and photodiode array detector DAD-3000RS. After passing the photodiode array detector, the eluent flow was guided to a Varian 1200L (Varian Inc., Palo Alto, Calif.) triple quadrupole mass detector with electrospray ionization interface, operated in negative ionization mode. The voltage was adjusted to −4.5 kV, heated capillary temperature was 280° C., and sheath gas was compressed air, zero grade, for the negative ionization mode. The mass detector was used in scanning mode from 65 to 1500 atomic mass units. Data from the Varian 1200L mass detector was collected, compiled and analyzed using Varian's MS Workstation, v. 6.9, SP2. Compounds were separated on a Phenomenex™ C8 reverse phase column, size 150×2 mm, particle size 3 μm, pore size 100 Å. The mobile phase consisted of 2 components: Solvent A (0.5% ACS grade acetic acid in double-distilled de-ionized water, pH 3-3.5), and Solvent B (100% Acetonitrile). The mobile-phase flow was 0.20 mL/min, and a gradient mode was used for all analyses. The initial conditions of the gradient were 95% A and 5% B over 30 min the proportions of A and B continuously changed, reaching 5% A and 95% B, which was kept for the next 8 min. During the following 4 min, the ratio was brought to initial conditions. An 8 min equilibration interval was included between subsequent injections. $^1$H NMR spectra were recorded in methanol-d4 on a 500 Varian VNMRS 500 MHz.

Optimization and Reproducibility of Extraction.

*Moringa* extract was prepared in ratios of 1:2, 1:5, and 1:10 (g of fresh leaves: mL water) for optimization of MIC content and percent yield. Triplicate samples of fresh *moringa* leaves (8 g) were ground in a coffee grinder, diluted accordingly in room temperature water and mixed for 30 min. For temperature experiments, fresh *moringa* leaves (8 g) were ground in a coffee grinder and added to water (40 mL) at 22, 40, 60, 80, and 100° C. as triplicate samples. The mixtures were maintained at these temperatures for 30 min in temperature-controlled water baths. Following 30 minutes of incubation, *moringa* extract was prepared as described herein. Analysis for percent yield (weight of *moringa* extract as a percent of starting fresh weight of leaves) and MIC content were determined.

Once the optimum temperature (22° C.) and dilution factor (1:5) were established using micro preparations, larger batches of *moringa* extract were made using a Vitamix blender (200 g: 1000 mL). Triplicate samples of *moringa* extract prepared in this manner from three separate batches of *moringa* leaves were compared for reproducibility tests.

Compound Stability.

Triplicate 100 mg samples of optimized *moringa* extract were placed in a 37° C. dark incubator and subjected to LCMS analysis for quantification of MICs at 0, 18 and 30 days.

Characterization of Extract.

The optimized *moringa* extract preparation, prepared with 22° C. water at a ratio of fresh leaves to water of 1:5 (w/v) was additionally characterized for total polyphenol content (TP) and oxygen radical absorbance capacity (ORAC). Total polyphenols were quantified by the Folin-Ciocalteu method (Singleton & Rossi, 1965) and samples were read at 726 nm against a gallic acid standard curve. ORAC was determined as µM Trolox equivalents (TE) using fluorescein as the fluorescent probe and 2,2'-azobis(2-amidinopropane)dihydrochloride (AAPH) as a peroxyl radical generator in a procedure adapted from previously published methods (Prior et al., 2003).

Cell Culture.

All reagents were supplied from Sigma-Aldrich Co. (St. Louis, Mo.) unless otherwise noted. RAW 264.7 macrophages (ATCC TIB-71) were maintained in Dulbecco's modified Eagle's medium (Caisson, North Logan, Utah) supplemented with 100 U/mL penicillin, 100 µg/mL streptomycin, and 10% fetal bovine serum. Cells were incubated at 37° C. in a 5% $CO_2$ humidified atmosphere and subcultured by cell scraping. For experiments, RAW cells were plated at a density of $4 \times 10^5$ cells/mL in 24-well plates. Cells were incubated overnight (18 h), washed with warm 37° C. PBS, and medium was replaced fresh DMEM medium. Cells were pretreated with designated doses of *moringa* extract, MICs or vehicle (50% EtOH). Lipopolysaccharide (1 µg/mL) was added after 2 h incubation with treatments to elicit inflammatory responses. Cells were treated in duplicate or triplicate. After an additional 6 h incubation period, media were collected and cells were washed with PBS prior to collection in TRIzol® Reagent (Ambion, Life Technologies). Samples were stored at −80° C. prior to processing.

Gene Expression Analyses.

Total RNA was extracted from cells according to manufacturer's specifications. Briefly, 200 µL of chloroform was added to 600 µL of TRIzol-harvested samples. Samples were vigorously mixed for 30 s, incubated at room temperature for 5 min, and centrifuged at 12,400 g Eppendorf tube and isopropanol was added to the aqueous phase to obtain a ratio of 7:10 supernatant to isopropanol. Samples were mixed by inverting, vortexed briefly and incubated for 10 min at −20° C. Samples were centrifuged at 12,400 g for 15 min at 4° C. Next, supernatant was removed and each sample was washed twice with 75% ethanol and centrifuged at 6000 g for 10 min. Samples were allowed to dry and resuspended in diethylpyrocarbonate (DEPC)-treated-water. RNA integrity was evaluated by running about 1 µg of RNA on a 1% agarose gel.

RNA was then treated with Deoxyribonuclease I (DNAse I) Amplification grade (Invitrogen), following the manufacturer's guidelines. RNA quality was checked on the NanoDrop 1000 system (NanoDrop Technologies). A ratio of OD 260:280≥2.0 and OD 260:230≥1.8 was considered to be good quality RNA. First-strand cDNA synthesis was performed using the ABI High-Capacity cDNA Reverse Transcription kit (Applied Biosystems, Foster City, Calif.) with RNAse I inhibitor, according to the manufacturer's instructions, using 1 µg of RNA. The thermal cycle program was set as follows: 10 min, 25° C.; 60 min, 37° C.; 60 min, 37° C.; 5 s, 85° C.; and final hold at 4° C.

Synthesized cDNAs were diluted 25-fold and 5 µL of dilution was used for qPCR with 12.5 µL of Power SYBR Green PCR master mix (Applied Biosystems), 0.5 µL primers (6 µM) and BPC grade water (Sigma) to a final reaction volume of 25 µL. Exon-spanning primer sequences were designed on Primer Express® (Life Tech) and are as follows: β-actin forward 5'-AAC CGT GAA AAG ATG ACC CAG AT-3' (SEQ ID NO: 1), reverse: 5'-CAC AGC CTG GAT GGC TAC GT-3' (SEQ ID NO: 2), IL-1β forward 5'-CAA CCA ACA AGT GAT ATT CTC CAT-3' (SEQ ID NO: 3), reverse 5'-GAT CCA CAC TCT CCA GCT GCA-3' (SEQ ID NO: 4), iNOS forward 5'-CCC TCC TGA TCT TGT GTT GGA-3' (SEQ ID NO: 5), reverse 5'-TCA ACC CGA GCT CCT GGA A-3' (SEQ ID NO: 6), COX-2 forward 5'-TGG TGC CTG GTC TGA TGA TG-3' (SEQ ID NO: 7), reverse 5'-GTG GTA ACC GCT CAG GTG TTG-3' (SEQ ID NO: 8), TNF-α forward 5'-TGG GAG TAG ACA AGG TAC AAC CC-3' (SEQ ID NO: 9), reverse 5'-CAT CTT CTC AAA ATT CGA GTG ACA A-3' (SEQ ID NO: 10), IL-6 forward 5'-TCG GAG GCT TAA TTA CAC ATG TTC-3' (SEQ ID NO: 11), reverse 5' TGC CAT TGC ACA ACT CTT TTC T-3' (SEQ ID NO: 12). All primers were validated by analyzing amplification efficiencies and melt-curve profiles.

Quantitative PCR amplifications were performed on an ABI 7300 Real-Time PCR System (Applied Biosystems) with the following thermal cycler profile: 2 minutes, 50° C.; 10 minutes, 95° C.; 15 seconds, 95° C.; 1 minute, 60° C. for the dissociation stage; 15 seconds, 95° C.; 1 minutes, 60° C.; and 15 seconds, 95° C. Inflammatory marker mRNA expressions were validated and samples were analyzed by the comparative ΔΔCt method and normalized with respect to the average Ct value of β-actin. Vehicle with LPS served as the calibrator for ΔΔCt analysis and was assigned a value of 1.0. Lower values indicate inhibition of gene expression relative to vehicle treated with LPS control. All experimental samples were run in triplicate and each reaction plate included no-template controls.

TNF-α Secretion Analysis.

RAW 264.7 macrophages were cultured and treated with *moringa* extract or MICs as stated above. After treatments, 1 mL of media was collected and immediately centrifuged at 13,500 g at 4° C. for 10 minutes. The supernatant was preserved at −80° C. until further processing with the BD OptEIA™ Mouse TNF ELISA kit (BD Bioscience, San Jose, Calif.) following the manufacturer's protocol. All the samples were assayed in duplicate. TNF-α levels were quantified using a reference standard curve provided with the kit. Absorbance was read at 450 nm and corrected at 570 nm.

Nitric Oxide Production Analysis.

RAW 264.7 macrophages were cultured and treated with *moringa* extract or MICs as stated herein. After treatments, 1 mL of media was collected and assayed in duplicate following the Griess Reagent System provided by Promega (Promega Corporation; Madison, Wis.). The nitrite standard (0.1 M sodium nitrite) reference curve was built performing a serial dilution (0 to 100 µM). Absorbance was read at 540 nm.

Cell Viability.

The effect of the treatments on cell viability was measured using MTT [3-(4,5-dimethyl-2-thiazolyl)-2,5-diphenyltetrazolium bromide] (TCI, Portland, Oreg.) (Mosmann, 1983). MTT (5 mg/mL) was dissolved in PBS (Cayman Chemical, Ann Arbor, Mich.), filtered through a 0.22 µm membrane and added to treated cells during the last 3-4 hours of treatment. Media were carefully aspirated and cells were dissolved in DMSO. The absorbance was read at 570 nm.

Statistical Analysis.

Data were expressed as mean±SEM. Statistical comparisons for optimization experiments were made by use of 1-way analysis of variance (ANOVA) followed Tukey's post-hoc test in the *moringa* extract optimization and stability experiments. Statistical comparisons for anti-inflammatory experiments were made by use of ANOVA followed by a Dunnett's or Wilcoxon test, as indicated, and $p<0.05$ were considered significant. *=$p<0.001$, =$p<0.01$, *=$p<0.05$. For statistical analysis, GraphPad Prism version 6.02 for Windows (GraphPad Software, Inc.) was used.

Example 2—Optimization of Extraction Method

Figure 2:
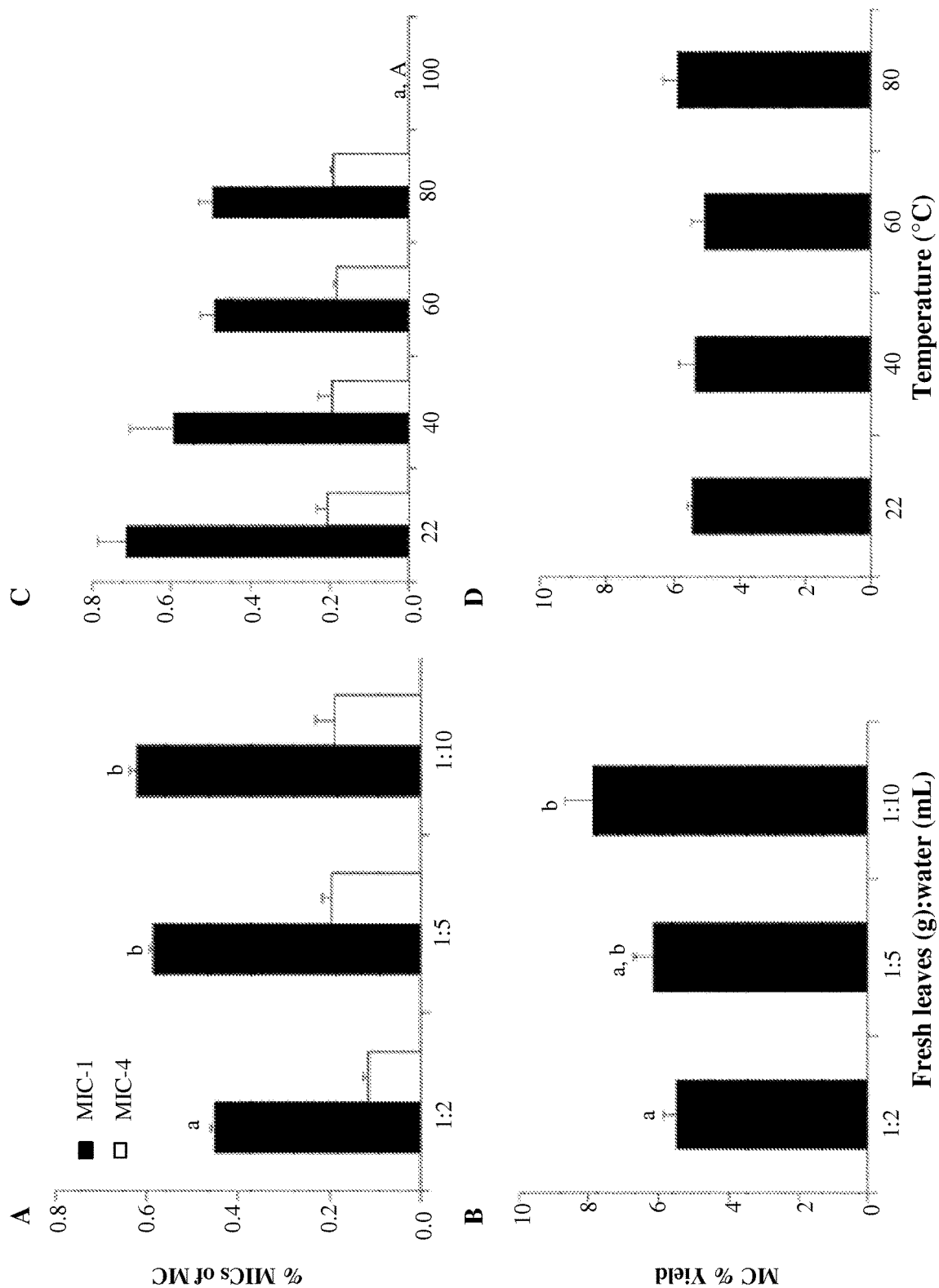
FIG. 2 shows the effect of dilution factor and temperature on isothiocyanate (MIC) content and percent yield in *M. oleifera* extract preparation. A. Effect of dilution ratio of fresh leaves (g):water (mL) on MIC concentration (mg of MIC/100 mg of extract). B. Effect of dilution ratio on extract percent yield (mg of extract/100 mg of fresh leaves). C. Effect of temperature on MIC concentrations (mg of MIC/100 mg of extract). D. Effect on temperature on extract percent yield (mg of extract/100 mg of fresh leaves).

Experiments were performed to optimize the in situ biotransformation of MGLs into MICs by myrosinase and to maximize the yield of MICs present in fresh leaves. The solvent ratio (weight of fresh leaves to volume of water) and temperature (22-100° C.) were tested to determine the optimal conditions for *moringa* extract yield and MICs content. The solvent ratio affected both the concentrations of MICs and the percent yield (FIGS. 2A & 2B). The 1:2 solvent ratio resulted in a lower average MIC-1 content (0.45% of *moringa* extract) compared with the 1:5 and 1:10 dilution, (0.59% and 0.62% of *moringa* extract, respectively). The amount of MIC-4 was higher in the 1:5 and 1:10 dilutions, but not to a statistically significant degree (0.12% of *moringa* extract compared with 0.20%, 0.19% respectively). Larger dilutions resulted in a proportional percent yield increase of *moringa* extract: (1:2) 5.47%, (1:5) 6.13%, (1:10) 7.87%. The 1:5 dilution factor was selected as optimum to maximize the amount of MICs captured in *moringa* extract, while minimizing the amount of water used for extraction.

Figure 3:
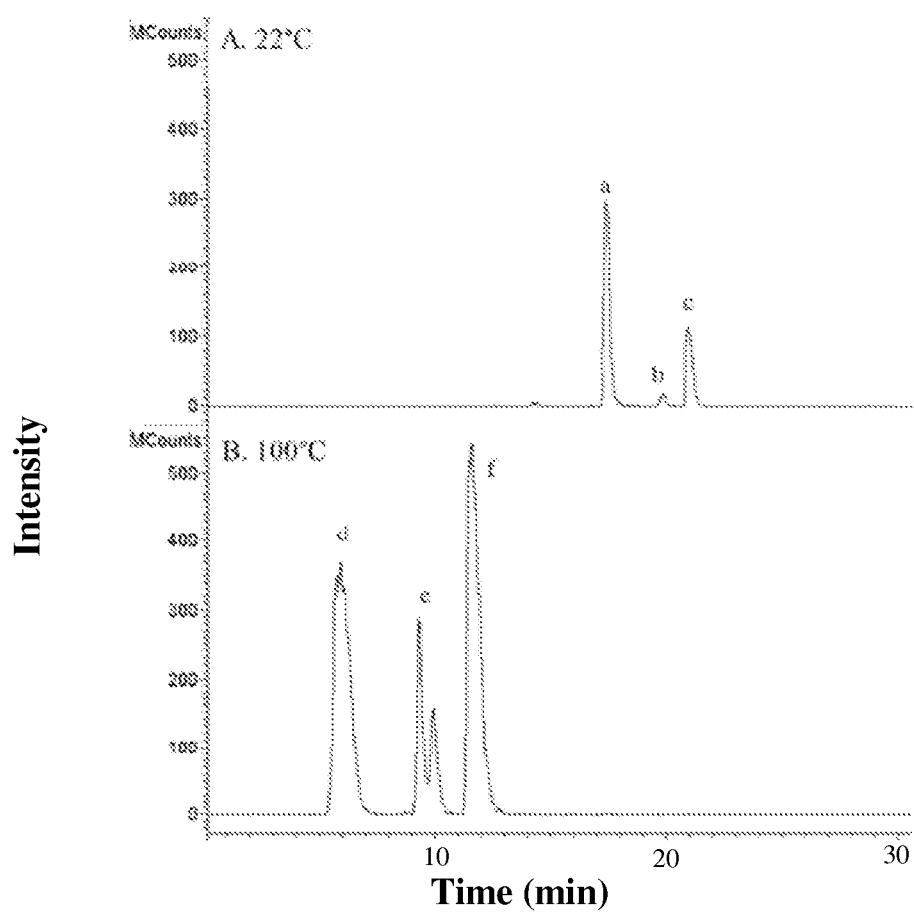
FIG. 3 provides a mass chromatogram of *moringa* glucosinolates (MGLs) and *moringa* isothiocyanates (MICs) at (A) 22° C. and (B) 100° C.

The 1:5 solvent ratio was used in the evaluation of the effect of water temperature on MIC concentration and percent yield. There was a significant difference in the amount of MICs extracted at water temperatures between 22 to 80° C. (MIC-1: 0.49-0.72% of *moringa* extract, MIC-4: 0.19-0.21% of *moringa* extract) with undetectable amounts at 100° C. (FIG. 2C). The LCMS mass chromatogram of MGLs and MICs in a 22° C. and 100° C. extraction shows the heat sensitivity of myrosinase activity at high temperatures (FIG. 3). At 22° C. myrosinase converted significant quantities of MGLs to MICs. At 100° C. myrosinase was inactivated and MGLs were not converted to their respective MICs. The thermal stability of *moringa* myrosinase is similar to broccoli myrosinase, with a reported thermal stability to 50-60° C. (Eylen, Oey, Hendrickx, & Loey, 2008) and complete destruction of the enzyme above 80° C. (Gallaher, Gallaher, & Peterson, 2012). Extraction with the 1:5 solvent ratio at room temperature (22° C.) was adopted to maintain full enzymatic conversion of MGLs into MICs.

Once *moringa* extract preparation had been optimized over temperature and solvent ratio, larger scale production of *moringa* extract required the use of a blender instead of a coffee grinder. This unintended parameter of scaling up the extraction resulted in a significant increase in MIC content. Under the same conditions, 1:5 solvent ratio at 22° C., the coffee grinder produced a lower amount of MIC-1 and MIC-4, approximately 1.00% total, in *moringa* extract while the blender increase the concentration of total MICs to 1.66% of *moringa* extract. This was likely due to finer fractionating of the leaves and the presence of water at the time of blending rather than grinding prior to combining with water in the case of the coffee grinder. Use of the blender, like use of the coffee grinder, did not create the harsh conditions of pulverization and not characteristic of prior art methods. It is expected that fine chopping of plant materials (e.g., use of or cutting or slicing implement moving at blender speeds) at lower temperatures (e.g., 4° C. to 60° C. or 80° C.) will yield significant quantities of MICs from *moringa* plant materials.

Preparation of *moringa* extract using the blender was performed with three separate batches of *moringa* leaves and subjected to MIC quantification by LCMS to ensure reproducibility of the extraction method. The content of MICs in *moringa* extract (1.66%) is approximately 3 times higher than the SF content obtained from broccoli sprouts (calculated by a reported 61% conversion rate of glucoraphanin to SF and converted to dry weight factoring 89% moisture content (Force, O'Hare, Wong, & Irving, 2007; Pereira et al., 2002; Song & Thornalley, 2007). *Moringa* extracts, prepared in large batches, were subsequently evaluated for chemical stability of MICs, total polyphenol content, oxygen radical absorbance capacity and anti-inflammatory activity in vitro.

Stability of Compounds.

Figure 4:
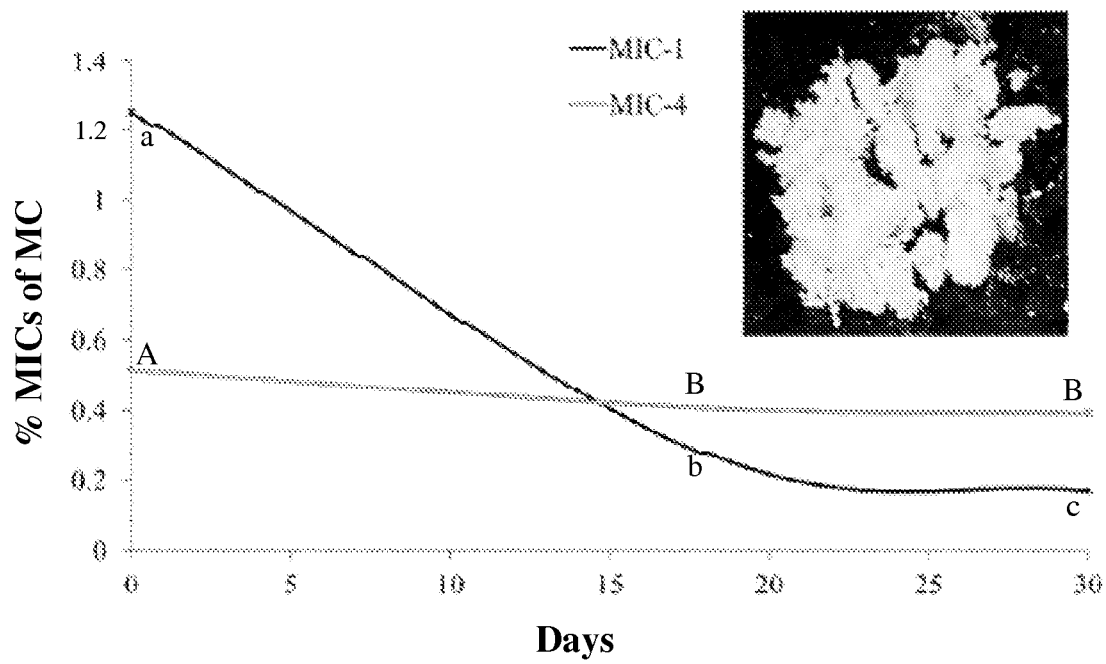
FIG. 4 shows the effect of storage of extract at 37° C. on isothiocyanate (MIC) stability.

The accelerated stability studies of MICs in *moringa* extract at 37° C. for 30 days showed approximately 80% and 20% degradation of MIC-1 and MIC-4, respectively (FIG. 4) compared to day 0. The higher stability of MIC-4 may be due to the monoacetylation at the 4' position of the rhamnose sugar. Greater acetylation is known to increase the stability of glycosylated molecules such as anthocyanins (Giusti & Wrolstad, 2003). However, both MIC-1 and MIC-4 demonstrated superior stability compared to reported values of SF, the main broccoli isothiocyanate, which degraded by 75% after 6 days at 37° C. (Franklin et al., 2013). SF is a volatile, viscous liquid, whereas MICs obtained by the methods disclosed herein are solids at room temperature. This is may be due to the higher molecular weight and rhamnose substitution compared with SF.

Total Polyphenol Content.

Total polyphenol (TP) content of *moringa* extract, determined by the Foling Ciocalteu method (Singleton & Rossi, 1965) was 3.82 mg of gallic acid equivalents per 100 mg of *moringa* extract (±0.22), which is similar to the reported TP content of dried *moringa* leaves (3.6 to 4.5% DW) (Sreelatha & Padma, 2009). This indicates that the aqueous *moringa* extract extraction methods disclosed herein captured the majority of polyphenols present in fresh leaves.

Predominant polyphenols identified in *moringa* include rutin, chlorogenic acid, and quercetin-malonyl-glucoside (Amaglo et al., 2010; Bennett et al., 2003). The molecular weights of these compounds were detected by LCMS analyses of *moringa* extract, but quantification of specific polyphenols was not performed.

Oxygen Radical Absorbance Capacity.

The ORAC value of *moringa* extract was 3.6 mmol Trolox equivalents (TE) per gram of *moringa* extract (±0.69 SEM). This is greater than reported values for spices with high ORAC, such as dried cinnamon powder (2.6 mmol TE per gram) (Wu et al., 2004). Fresh and dried *moringa* leaves were previously reported to contain high levels of antioxidant compounds, including phenolics, flavonols, carotenoids and ascorbic acid (Siddhuraju & Becker, 2003; Dillard & German, 2000). Antioxidants in various *moringa* leaf extracts (total polyphenols, total flavonoids) have been shown in vitro to possess free-radical scavenging activity and ferric-reducing power (Vongsak et al., 2012). In vivo *moringa* extracts have also been shown to increase the antioxidant activity of reduced glutathione, superoxide dismutase, and catalase, while decreasing lipid peroxidation (Moyo, Oyedemi, Masika, & Muchenje, 2012).

*Moringa*'s antioxidant capacity has primarily been attributed to the presence of polyphenols and flavonoids, while little attention has been paid to the antioxidant potential of MGLs and MICs present in *moringa* extracts. Yet, isothiocyanates (ITCs) from crucifers have been shown to possess strong antioxidant activity. SF, the primary ITC in broccoli, is one of the most potent inducers of phase II enzymes (Traka & Mithen, 2009). Reduction of oxidants has been correlated with reduced pathogenesis of inflammation (Geronikaki & Gavalas, 2006).

Example 3—*Moringa* Extracts Demonstrate Anti-Inflammatory Activity

Figure 5:
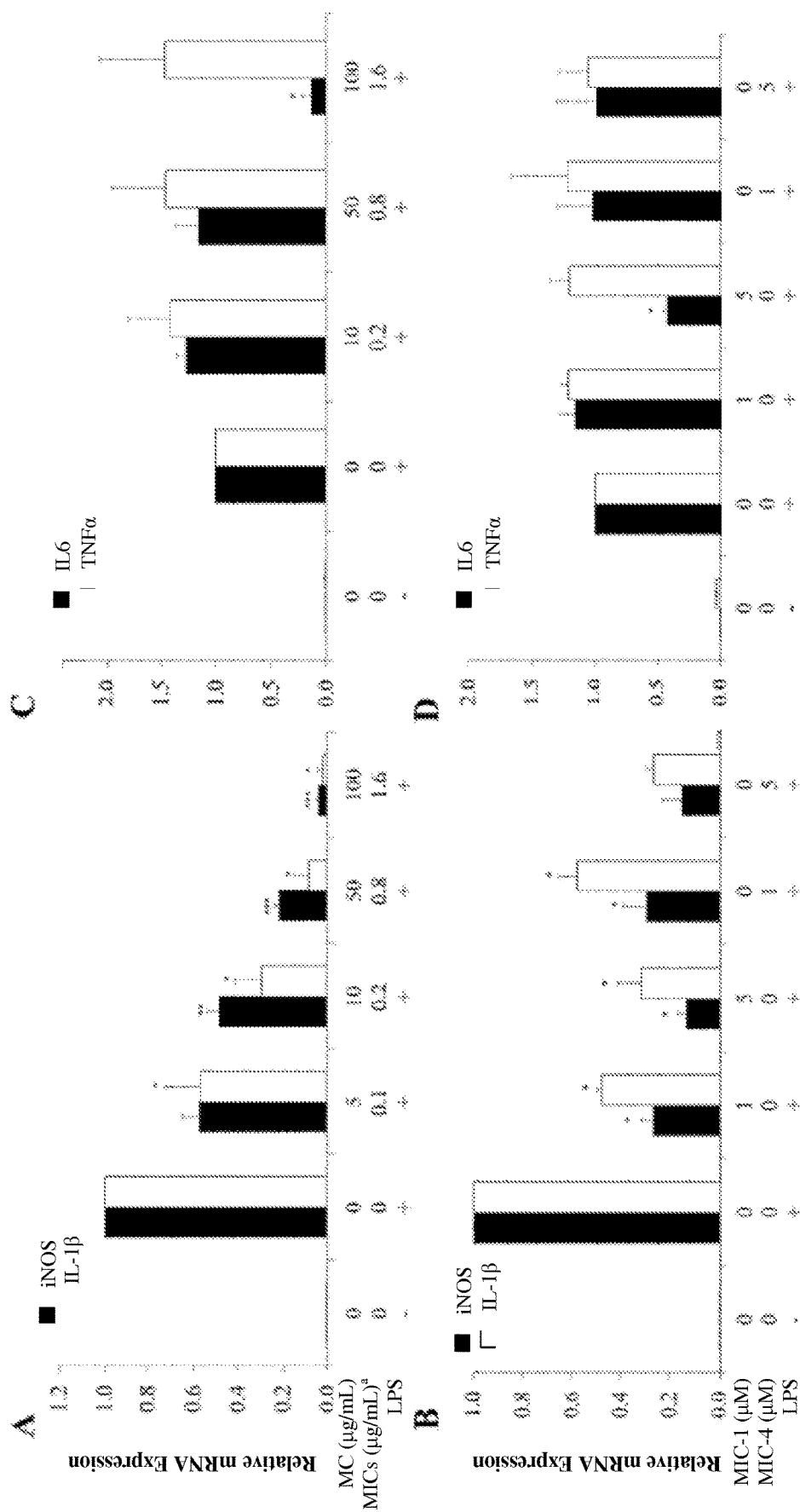
FIG. 5 shows the anti-inflammatory effects of a *moringa* extract produced by the methods described herein, MIC-1, and MIC-4 on LPS-induced iNOS, IL-1β, IL-6 and TNF-α gene expression in RAW 264.7 macrophage cells. Cells were pretreated for 2 hours with *moringa* extract or MICs and then induced with LPS for κ hours. Values show relative gene expression compared to vehicle with LPS control, as determined by comparative ΔΔCt analysis. A: Effect of *moringa* extract on iNOS and IL-1β. B: Effect of *moringa* extract on LPS-induced IL-6 and TNF-α. In A and B MIC$^a$ indicates the corresponding MIC concentration present in *moringa* extract at the given doses. 1.6 µg/uL of MICs in the 100 µg/uL *moringa* extract treatment corresponds to a MIC concentration of 5.5 µM (4 µM MIC-1 and 1.5 µM MIC-4). C: Effect of *moringa* extract on IL-6 and TNF-α. D: Effect of MICs on LPS-induced IL-6 and TNF-α.

*Moringa* extract produced by the methods disclosed herein demonstrated a dose dependent inhibitory effect on iNOS and IL-1β gene expression in RAW 264.7 macrophages in vitro (FIG. 5A). Tested concentrations of *moringa* extracts ranged from 5 to 100 µg/mL (0.1% to 1.6% MIC content). The molar concentration of MICs in *moringa* extract at the various doses ranged from approximately 0.28 µM to 5.5 µM. Almost complete suppression of iNOS and IL-1β gene expression was observed at 100 µg/mL of *moringa* extract (5.5 µM MIC content).

Purified MIC-1 and MIC-4 tested at 1 and 5 µM concentrations also showed significant reduction of mRNA expression of iNOS and IL-1β (FIG. 5B). Additionally, *moringa* extract at 100 µg/mL (FIG. 5C) and MIC-1 at 5 µM (FIG. 5D) were able to decrease IL-6 gene expression significantly. However, no reduction of TNF-α gene expression was seen at any of the concentrations of *moringa* extract, MIC-1 and MIC-4 tested.

Nitric oxide (NO) and TNF-α cytokine production were reduced by *moringa* extract, MIC-1 and MIC-4 (FIGS. 6 A & B). *Moringa* extract at 100 µg/mL, containing 1.15% MIC-1 and 0.51% MIC-4, inhibited TNF-α production by 70% compared to the control. MIC-1 and MIC-4 at 5 µM reduced TNF-α production by 20% and 27%, respectively. The enhanced anti-inflammatory activity of *moringa* extract compared with MIC-1 and MIC-4 alone could be the result of additive or synergistic activities of *moringa* extract polyphenols or could be the presence of less abundant, but perhaps highly active MIC-2 and MIC-3. These results demonstrate the plausible advantage of delivering MICs in a food-grade product. TNF-α RNA expression was not significantly inhibited by *moringa* extract, MIC-1, or MIC-4, indicating that *moringa* phytochemicals may inhibit TNF-α production at the translational level or at the level of TNF-α turnover.

Figure 6:
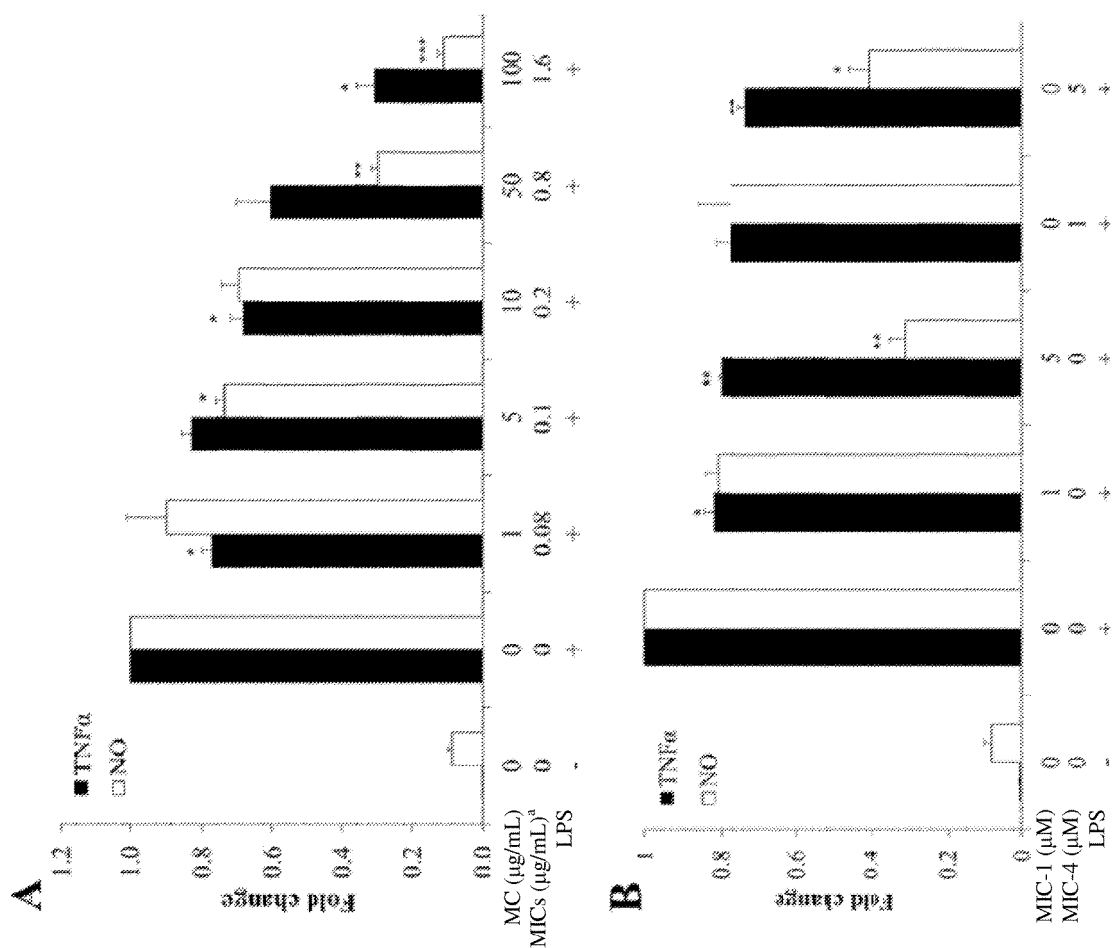
FIG. 6. Body weight gain (A), ratio of accumulated food intake to body weight (B), fat mass (C) and free fat mass (D) in VHFD and VHFD+5% *moringa* extract-fed mice. n=12 mice per group, Data are means±SEM. Comparisons to controls were made by Welch's test. *P<0.05; P<0.01; *P<0.001.

*Moringa* extract, MIC-1 and MIC-4 inhibited the production of NO significantly (FIGS. 6 A & B). This is consistent with previously reported NO inhibition by MIC-1 and MIC-4 (IC50 of 14.43 and 2.71 µM, respectively) (Cheenpracha et al., 2010). *Moringa* extract, at 100 µg/mL, was able to inhibit NO formation by 90%. MIC-1 and MIC-4 are at least partially responsible for this effect, because they inhibited NO formation at 5 µM. *Moringa* extract also contains MIC-2 and MIC-3, reported to inhibit NO formation at low micromolar concentrations (IC50 of 1.67 µM and 2.66 µM, respectively (Park et al., 2011)). *Moringa* extract, MIC-1 and MIC-4 showed no signs of cytotoxicity at the concentrations tested in anti-inflammatory assays, as demonstrated in MTT-based cell viability assays.

Example 4—Additional Parameters for Preparation of *Moringa* Plant Compositions and Extracts

*Moringa* plant compositions and extracts are prepared in a variety of ways to accommodate situations where outdoor cultivation or manufacturing equipment is limiting. For example, *moringa* can be grown indoors as sprouts (5-10 days old) and readily used for the preparation of *moringa* extract. Fresh *moringa* leaves can be injured without the addition of water, by blending or rolling, to activate myrosinase and convert MGLs to MICs. This injured material can be easily dried, sold as is, or shipped for further extraction/concentration of MICs. Alternatively *moringa* extract can be made in a 1:1 dilution to increase the concentration of MICs, while still allowing for rapid drying (solar/oven dryers). Provided below in Table 1 is a list of various methods of extraction and filtration performed and percent yield (product dry weight as a percent of the starting fresh weight), % MIC-1 (as determined by LCMS as a percent of product dry weight), % MIC-4 (as determined by LCMS as a percent of product dry weight) and MIC-4:MIC-1 ratio of the resulting plant compositions and extracts.

TABLE 1

| Method of Extraction & Separation | % Yield[a] | % MIC-1[b] | % MIC-4[b] | MIC-4:MIC-1 Ratio |
|---|---|---|---|---|
| Commercial *Moringa* Dried-Leaf Powder (Moringa Farms, CA) | 20-25 | 0.03 | 0.002 | 0.05 |
| Blended[c], No Water | 20-25 | 0.25 | 0.07 | 0.3 |
| Rolled[d], No Water | 20-25 | 0.31 | 0.06 | 0.2 |
| Blended, No Water, Filtered[e] | 1.6 | 0.19 | 0.18 | 0.9 |
| Blended 1:1 Dilution, Filtered & Centrifuged[g] | 4.0 | 0.23 | 0.06 | 0.3 |
| Blended 1:1 Dilution[f], Filtered | 4.5 | 0.37 | 0.17 | 0.5 |
| Blended 1:1 Dilution, Juiced[h] | 3.9 | 0.42 | 0.34 | 0.8 |
| Blended 1:5 Dilution, Filtered & Centrifuged | 6.1 | 1.04 | 0.46 | 0.4 |

TABLE 1-continued

| Method of Extraction & Separation | % Yield[a] | % MIC-1[b] | % MIC-4[b] | MIC-4:MIC-1 Ratio |
|---|---|---|---|---|
| Blended 1:5 Dilution, Filtered | 9.4 | 1.08 | 1.91 | 1.7 |
| Blended 1:5 Dilution, Juiced | 7.7 | 2.16 | 3.18 | 1.5 |

[a]Product dry weight as a percent of starting fresh weight
[b]Amount of MIC-1/MIC-4 determined by LCMS as a percent of product dry weight
[c]Leaves were ground in a blender (Vitamix 5200 Blender, Cleveland, OH)
[d]Leaves were placed on a screen and crushed with a rolling pin
[e]Filtered using Miracloth (Calibiochem, Billerica, MA) and hand squeezed
[f]Dilution faction is stated as the ratio of fresh leaves used (g): amount of water used (mL)
[g]Centrifuged for 10 min at 3200 g and 4° C.
[h]Mixture was placed in a Juicer (Jack LaLanne's Ultimate Power Juicer, Fairfield, NJ)

A 1:5 dilution ratio provided a significantly higher concentration of MICs compared to the 1:1 dilution ratio. The best preparation method for the 1:5 ratio was determined to be blending, followed by juicing. Centrifugation in all cases led to lower levels of MIC-4, the more stable MIC and is thus not recommended. Drying the 1:5 ratio preparations can be achieved by rotoevaporation, followed by freeze-drying or spray drying. The 1:5 ratio preparations were subjected to rotoevaporation for 1 hour at 50° C. which removed approximately 75% of the water. This increased the solid concentration to levels required for spray drying. No significant loss of either MIC-1 or MIC-4 was observed under rotoevaporation conditions when compared to samples that were freeze-dried. Further concentration of MICs and removal of sugars from the extract can also be performed with solid phase-extraction (SPE).

Example 5—Additional Extraction Method

Fresh *moringa* leaves were injured (e.g., crushed with mortar and pestle) to bioconvert MGLs to MICs and then dried at 37° C. for 18 hours. The resulting injured and dried plant material can be used in this condition as a product with enhanced MIC content or stored/shipped and processed at a later date by extraction for further concentration of MICs. Extraction of these crushed-dried leaves in a 1:5 ratio (g of fresh weight equivalents:mL of water) resulted in a MIC-1 content of 1.01% and MIC-4 content of 0.57%. This demonstrated bioconversion of MGLs to MICs in the crushing step, stability of MICs in the drying, storage and potential shipping step, and concentration of MICs in the extraction step. This procedure allows for spatial and temporal separation between a supply of fresh *moringa* leaves and extraction concentration.

Example 6—Materials and Methods

Materials:
*Moringa* extract was produced by the methods disclosed herein. Food formulation for the experiments provided in Example 7 was standardized to deliver 800 mg of MICs/kg of food. In the long-term study, a very high-fat diet (VHFD) (60% kcal from fat) contained 5% *moringa* extract (1.66% MIC by DW). The diet was formulated by Research Diets (New Brunswick, N.J.) to be isocaloric for fat, protein and carbohydrate content (Suppl. Table 1).

Animals:
Twenty-four male C57BL/6J mice at 5 weeks of age were obtained from Jackson Laboratories (Bar Harbor, Me.). Mice were acclimated for 9 days and housed 4 animals per cage under a 12-hour light/dark cycle, with ad libitum access to water and a VHFD or VHFD+5% *moringa* extract for twelve weeks. Body weight and food intake was recorded weekly. Food intake was estimated as follows: [total food consumed per cage]/[mice per cage]×[day of food consumption]. Body composition was determined at 4, 8, and 12 weeks by magnetic resonance imaging using an EchoMRI-100 instrument (Echo Medical Systems, Houston, Tex.). At the end of the study, mice were euthanized with carbon dioxide. Blood and tissues (liver, inguinal fat, gastrocnemius muscle and ileum) were collected immediately and preserved at −80° C.

Oral Glucose Tolerance Test (OGTT):
Mice in the three-month study were first fasted overnight before fasting glycemic levels were recorded using a glucometer (AlphaTRAK® 32004-02, Abbott Animal Health, Abbott Park, Ill.) and gavaged with 2 g/kg of glucose at weeks 4, 8 and 12 weeks of treatment. An additional six mice on the VHFD at the same age were gavaged with 300 mg/kg of metformin (positive control) 3 hours prior to glucose gavage. Glycemic levels were measured at intervals up to 120 minutes.

Acute OGTT:
Fifteen male C57BL/6J mice were purchased, acclimated and housed as described in the 3-month study. Mice were fed ad libitum a VHFD for 12 weeks. The OGTT was performed as described above except for gavage treatments of 2 g/kg of *moringa* extract (n=6), water (vehicle; n=6), or 300 mg/kg of metformin (n=3).

Blood Chemistry Analysis:
Animals were fasted overnight and trunk blood was collected immediately after euthanization. Samples were collected in tubes with EDTA and plasma was aliquotted into cryovials and stored at −80° C. for analysis. Insulin, leptin, resistin, interleukin-1 beta (IL-1β) and tumor necrosis factor alpha (TNFα) were measured using a multiplex assay (Millipore, Temecula, Calif.) measured on a Luminex 200 (Luminex, Austin, Tex.). Total cholesterol and triglycerides (TG) were assayed on a DxC 600 Pro (Beckman Coulter, Inc., Indianapolis Ind.).

Liver Histology, Total Lipid Extraction, and TG Levels:
Randomly selected liver sections were fixed in 10% neutral-buffered formalin for 48 hours, then processed and embedded in Paraplast. Six-micrometer sections were cut and stained in hematoxylin and eosin. A diagnosis of fatty liver was made based on the presence of macro or microvesicular fat >5% of the hepatocytes in a given slide. Total lipid content of liver and feces was determined by Folch's method (19). Briefly, liver (about 300 mg) and feces (about 200 mg) were extracted 20:1 (v/w) with $CHC_{12}/CH_3OH$ (2:1), followed by solvent evaporation and DW calculation.

Gene Expression Analysis by Quantitative RT-PCR:
Liver and Ileum.
Total RNA was isolated from liver and ileum for TNFα, IL-1β, interleukin-6 (IL-6) expression; and additionally for glucose-6 phosphatase (G6P), PEPCK and glucokinase (GcK) expression from liver tissue using the PureLink® RNA mini kit plus on-column DNase treatment (Applied Biosystems, Foster City, Calif.). Tissue (100 mg) was homogenized with TRIzol® using zirconium beads in a Bead Bug homogenizer (Benchmark Scientific, Inc. Edison, N.J.). First-strand cDNA was synthetized from 2 μg total RNA using the high capacity cDNA reverse transcription kit plus RNase inhibitor (Applied Biosystems) with oligo-d(T)s as primers. PCR analyses were performed on a 7300 Real-Time PCR system using the TaqMan Assays (Applied Biosystems). Hydroxymethylbilane synthase (Hmbs) was used to normalize target gene expression and effect of treatment on gene expression levels was evaluated by the ΔΔCt method (20).

In Vitro Gluconeogenesis Studies.

H4IIE rat hepatoma cells (CRL-1548, American Type Culture Collection, Manassas, Va.) were assayed for glucose production as previously described (21). Cell viability was measured by the 3-(4,5-Dimethyl-2-thiazolyl)-2,5-diphenyltetrazolium bromide (MTT; TCI, Portland, Oreg.) assay (22). RNA extraction, cDNA synthesis and qPCR for gene expression of PEPCK and G6P were performed as described above.

Example 7—*Moringa* Extract Reduced Body Weight and Fat Accumulation in Mice

This Example determined the effect of a *moringa* extract produced by the methods disclosed herein on body weight, body composition, OGTT, liver composition and lipid content of mice fed either a very high-fat diet (VHFD)+*moringa* extract or a VHFR without *moringa* extract (control).

The VHFD+5% *moringa* extract-fed mice gained significantly less weight over the 3-month study compared to the VHFD-control mice (P<0.001 from 4-12 weeks) with a final average weight of 38.4±1.0 g vs. 46.9±1.0 g (mean±SEM), respectively (FIG. 6A). All animals involved in the study looked healthy at the end of the study with no adverse effects noticed. Weekly food consumption remained stable throughout the 12-week study, averaging 2.22±0.02 g/day for the VHFD+5% *moringa* extract group versus 2.42±0.05 g/d for control mice. The 5% *moringa* extract diet contained 800 mg of MICs/kg. Therefore, the mice were consuming approximately 66 mg of MICs per day. Accumulated food intake only became significantly less in the VHFD+5% *moringa* extract-fed group at the 12th week (P<0.05). The ratio of accumulated food intake to body weight, however, was significantly higher in the VHFD+5% *moringa* extract-fed mice compared to the VHFD group throughout the entire study (FIG. 6B). Body composition at 4, 8 and 12 weeks showed lower fat accumulation (FIG. 6C) and greater free fat (lean mass) as a percentage of body weight in the VHFD+5% *moringa* extract-fed mice compared to the VHFD-fed mice (FIG. 6D).

Figure 7:
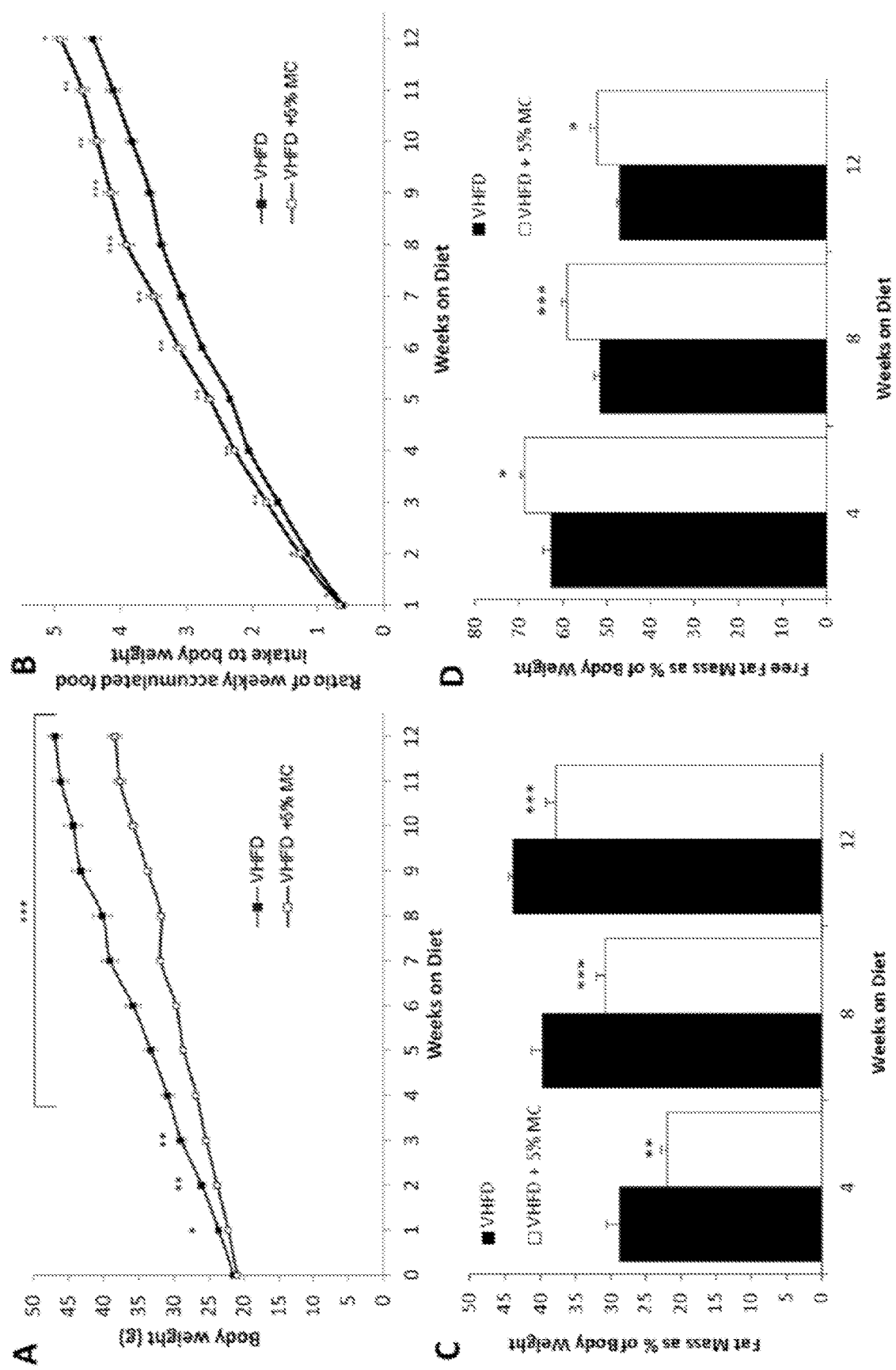
FIG. 7. Oral glucose tolerance test performed at 4 (A), 8 (B) and 12 (C) weeks on mice fed VHFD, VHFD+5% *moringa* extract, and on mice receiving VHDF gavaged with 300 mg/kg metformin on the day of OGTT. Area Under the Curve of OGTT at 4, 8, and 12 weeks (D). n=12 mice per group, except for metformin group where n=6 and only shown as a reference group. Data are means±SEM. Comparisons to controls were made by t-test. *P<0.05; P<0.01; *P<0.001 in comparison of VHFD and VHFD+5% *moringa* extract only.
Figure 8:
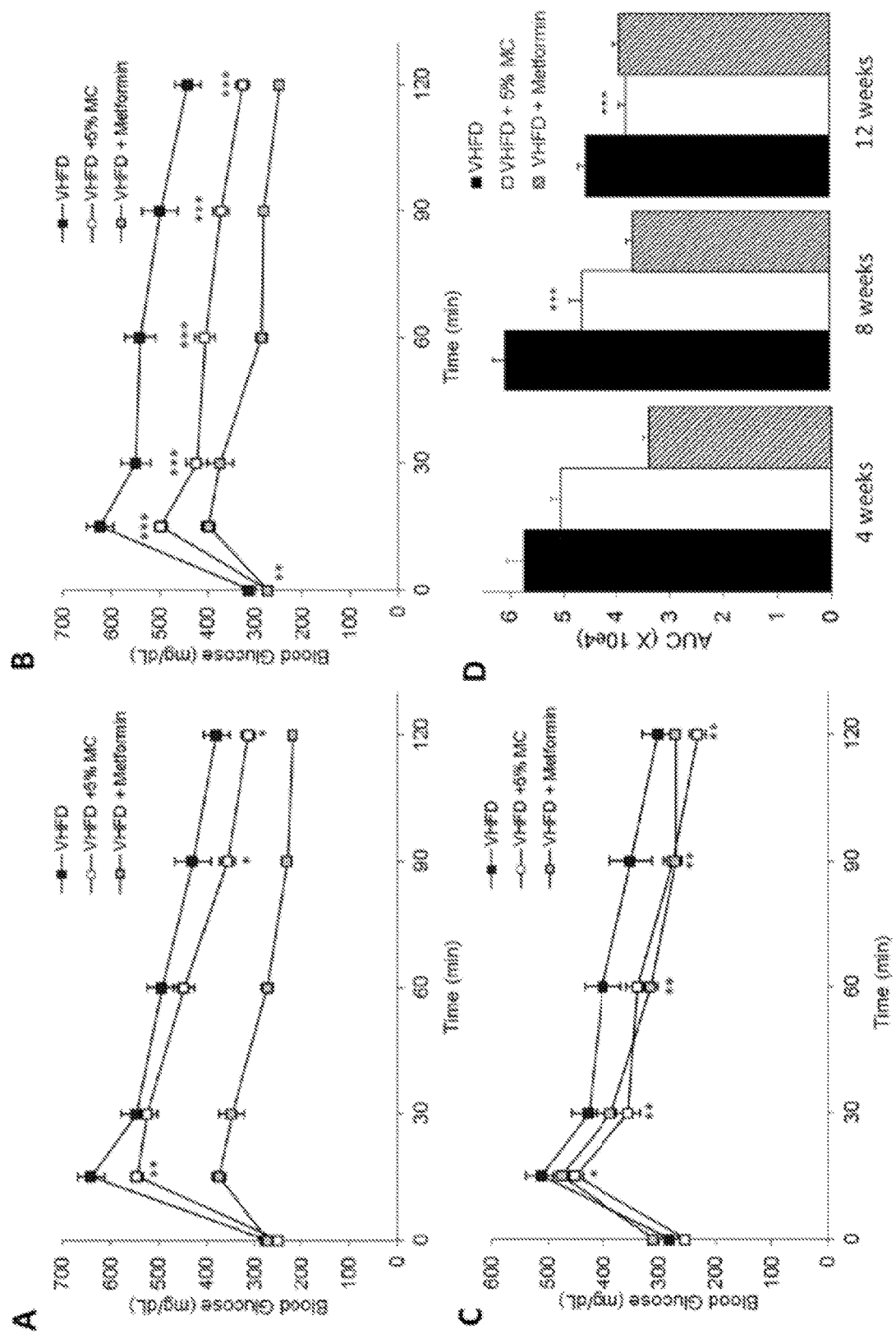
FIG. 8. Gross examination of liver samples from VHFD-fed mice (A) and VHFD+5% *moringa* extract-fed mice (B). Liver weight in VHFD and VHFD+5% *moringa* extract (n=12) (C) Data are means±SEM. **: p<0.01. Histological examination of liver samples from VHFD (D) and VHFD+ 5% *moringa* extract (E). Fat content in liver from VHFD-fed mice and VHFD+5% *moringa* extract-fed mice (n=12) (F). Comparisons to controls were made by Welch's test. Data are means±SEM. P<0.01; *P<0.001.

OGTT performed at 4, 8 and 12 weeks demonstrated lower blood-glucose levels and faster return to fasting levels in VHFD+5% *moringa* extract-fed mice compared to VHFD-fed mice (FIG. 7). Compared to fatty livers of VHFD-fed mice, livers from the VHFD+5% *moringa* extract-fed animals did not show the appearance of fatty-liver disease (FIGS. 8A and 8B) as also evident from the histological comparison (FIGS. 8D and 8E). The livers of VHFD+5% *moringa* extract-fed mice weighed less (FIG. 8C) and contained lower levels of lipids in relation to the VHFD-fed mice (FIG. 8F). There was no significant difference in the lipid content as a percent of dry fecal weight from the two experimental groups (VHFD, 0.47±0.14%; VHFD+5% *moringa* extract, 0.46±0.04%).

Effect of *Moringa* Extract on Blood Composition.

Figure 9:
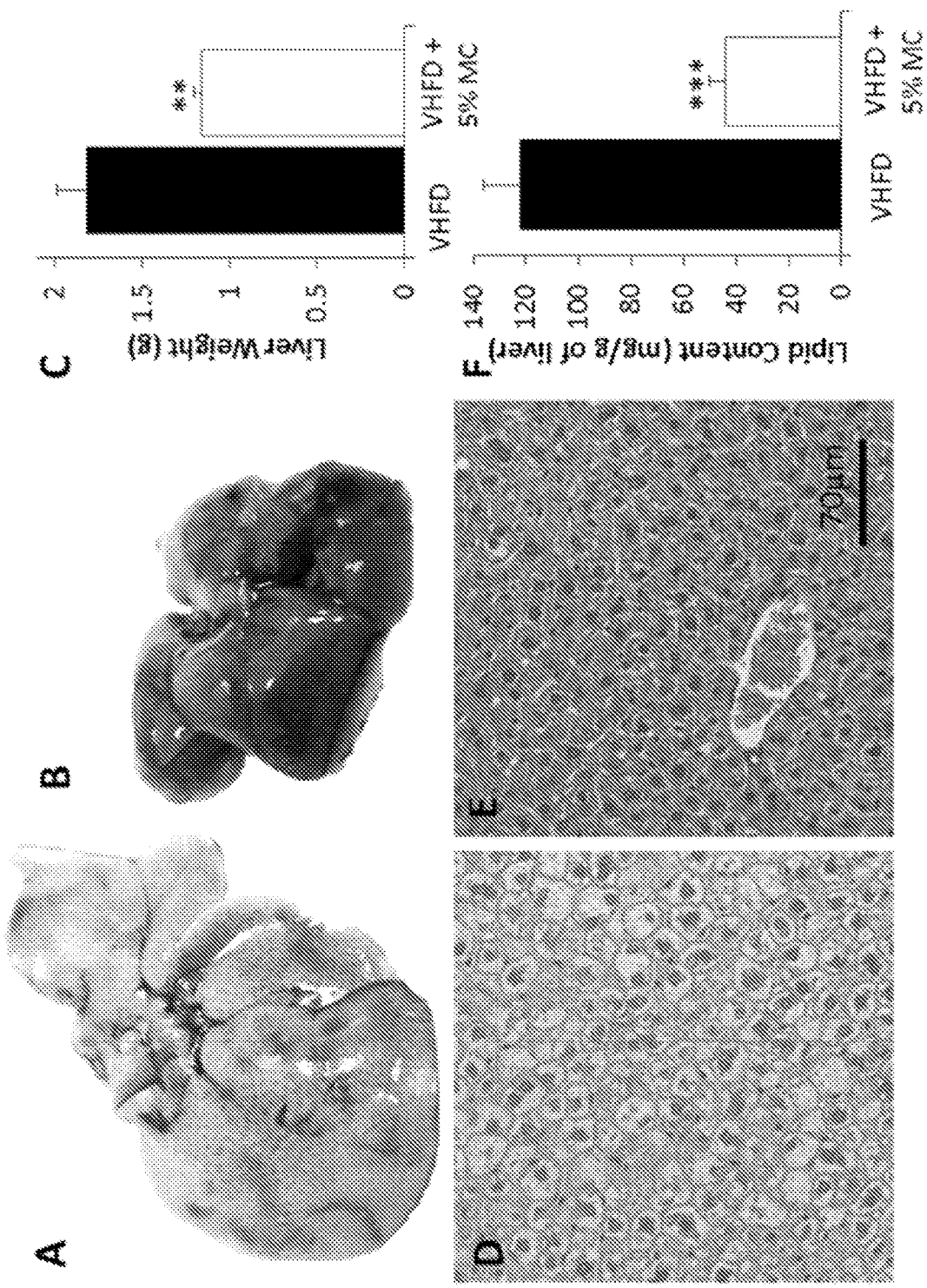
FIG. 9. Blood plasma expression of insulin, leptin, resistin (A), IL-1β, TNFα (B), total cholesterol and triglycerides (C) in VHFD and VHFD+5% *moringa* extract-fed mice. n=12 mice per group except for IL-1β and TNFα where n=5, undetectable levels below 2.4 pg/mL were excluded. Comparisons to controls were made by Welch's test. Data are means±SEM. *P<0.05; **P<0.01.
Figure 10:
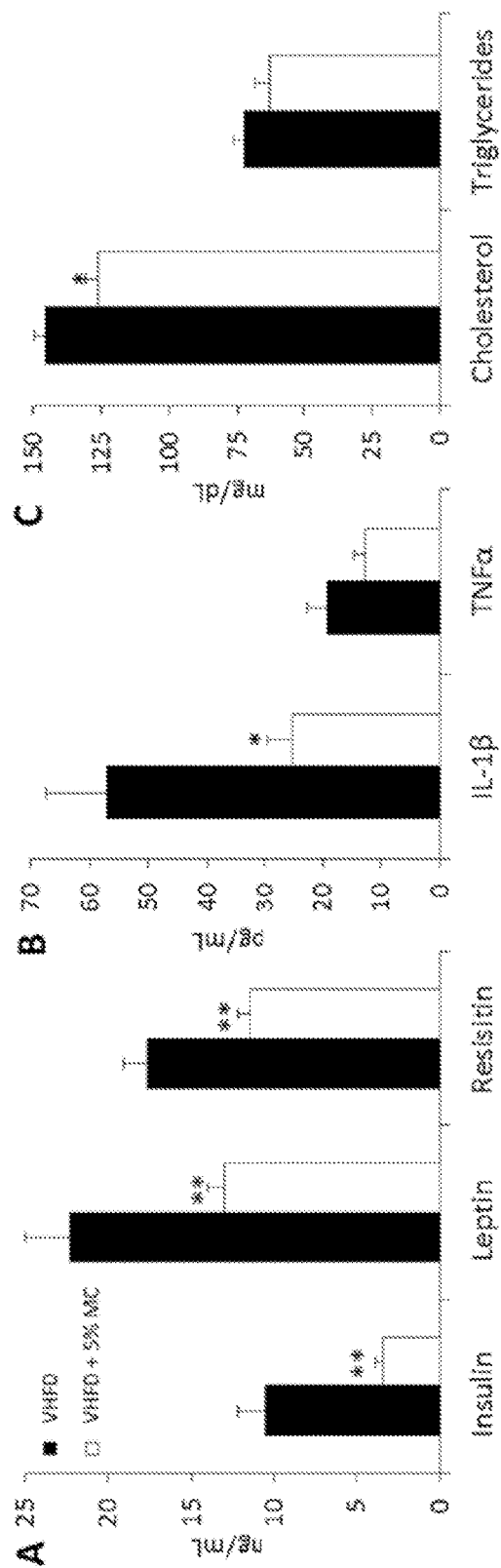
FIG. 10. Gene expression of inflammatory markers in liver (A) and ileum (B) of VHFD and VHFD+5% *moringa* extract-fed mice (n=12). Data are means±SEM. Comparisons to controls were made by Welch's test for liver and ileum. *P<0.05.

VHFD+5% *moringa* extract-fed mice had lower blood plasma levels of glucose regulators (insulin, leptin, resistin) (FIG. 9A), inflammatory cytokines (IL-1β and TNFα) (FIG. 9B), cholesterol and triglycerides (FIG. 9C) compared to the VHFD group. Reduced gene expression of pro-inflammatory markers, TNFα, IL-6, and IL-1β, were observed in the liver (FIG. 10A) and ileum (FIG. 10B) tissue from the VHFD+5% *moringa* extract-fed mice compared to the VHFD group.

Effect of *Moringa* Extract and MICs on Glucose Metabolism and OGTT.

Figure 11:
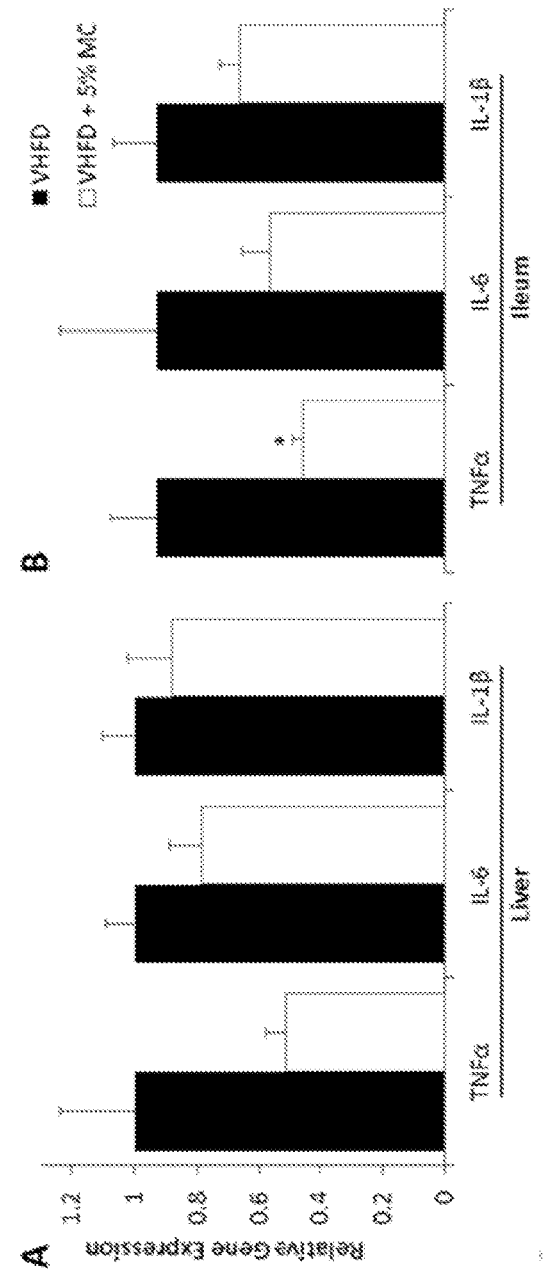
FIG. 11. Effects of *moringa* extract, MIC-1, MIC-4 and sulforaphane (SF) on glucose production (A, B) and gene expression of G6P and PEPCK in HII4E liver cells; n=3 (C). Expression of G6P and PEPCK in hepatic tissue of VHFD and VHFD+5% *moringa* extract-fed mice (D) n=12. Acute OGTT test in VHFD-fed mice gavaged with 2 g/kg of *moringa* extract. (E) n=6. Comparisons to controls were made by Dunnett's test for A and C, t-test for D and Welch's for E. Data are means±SEM. *: p<0.05, : p<0.01, *: p<0.001.

*Moringa* extract (produced by the methods disclosed herein) and MICs significantly reduced glucose production by approximately 60% in HII4E liver cells at 10 µg/mL and 1 µM, respectively (P<0.001). MIC-1 and MIC-4 demonstrated superior activity to SF at the same concentrations (FIG. 11A). To further explore the activity of MICs in comparison to the prescription drug metformin, MIC-4 and metformin were tested over a range of 5 concentrations, showing $IC_{50}$ of glucose production at 7 µM for MIC-4 versus 800 µM for metformin (FIG. 11B). *Moringa* extract and MICs also significantly decreased expression of G6P and PEPCK in HII4E liver cells relative to the vehicle (FIG. 11C). G6P expression was significantly lower in the hepatic tissue of VHFD+5% *moringa* extract-fed mice compared to the controls (FIG. 11D). Glucose lowering effects of *moringa* extract were further tested in vivo by the acute OGTT, to eliminate the weight difference variable in the long-term feeding study. The acute OGTT resulted in significantly lower blood glucose levels at 15 and 30 minutes in the *moringa* extract-gavaged mice (2 g/kg) compared to the vehicle (FIG. 11E).

Figure 12:
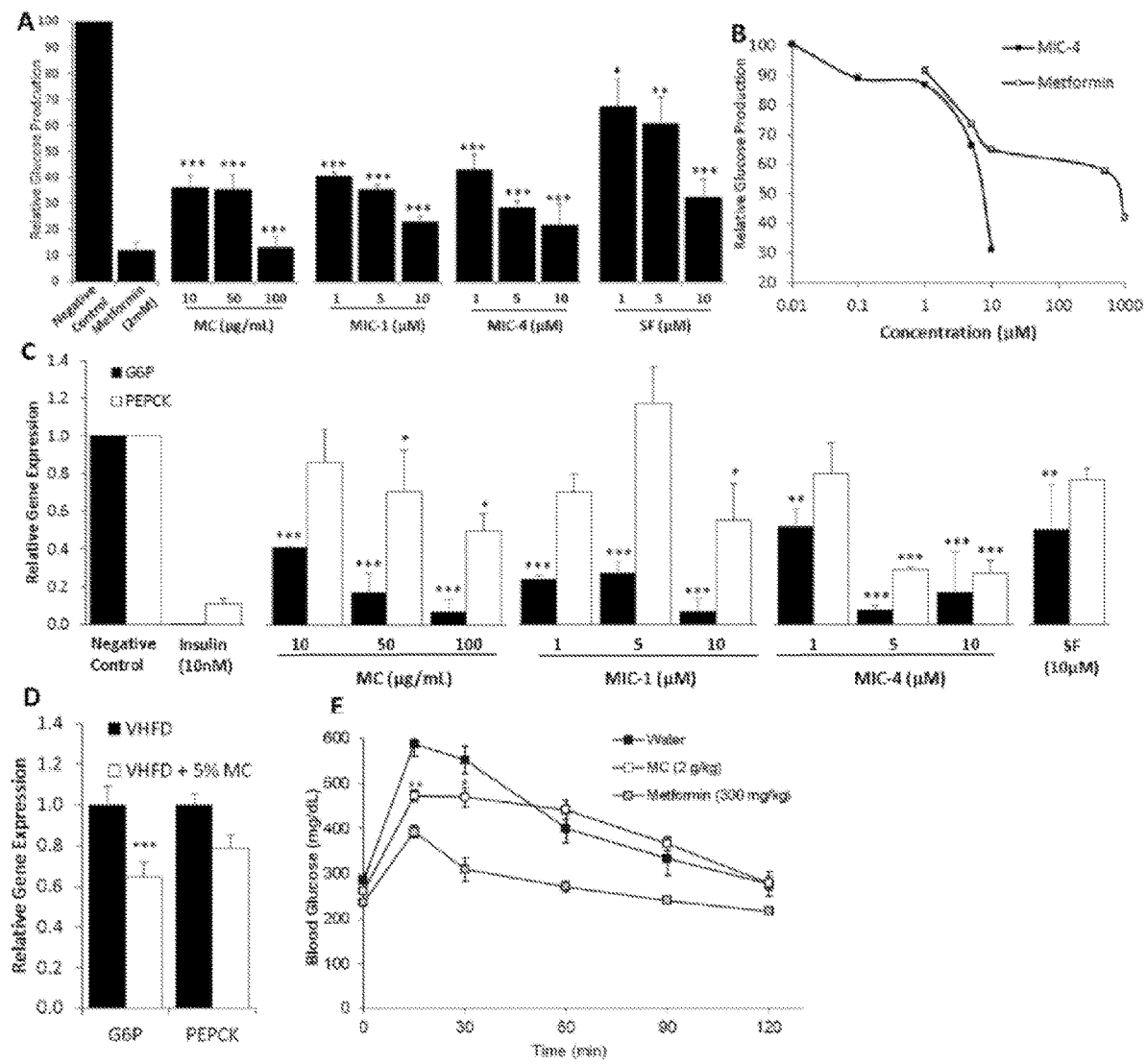
FIG. 12. Effects of MICs, SF and *moringa* extract on glucose metabolism in vitro (A, B, C) and in vivo (D, E). Effects of MC, MIC-1, MIC-4 and sulforaphane (SF) on glucose production (A, B) and gene expression of G6P and PEPCK in HII4E liver cells; n=3 (C). Expression of G6P and PEPCK in hepatic tissue of VHFD and VHFD+5% MC-fed mice (D) n=12. Acute OGTT test in VHFD-fed mice gavaged with 2 g/kg of MC (E) n=6. Comparisons to controls were made by Dunnett's test for A and C, t-test for D and Welch's for E. Data are means±SEM. *: p<0.05, : p<0.01, *: p<0.001.

This study provides justification and mechanistic evidence for the uses of *moringa* extract prepared as disclosed herein as a dietary agent in preventing type 2 diabetes by demonstrating that MIC-enriched *moringa* extract caused significant reduction in weight gain, hepatic adiposity, gluconeogenesis, insulin, cholesterol, and inflammatory markers. This study also establishes the role of MICs as primary anti-diabetic actives in *moringa* extract. The most notable result of the long-term feeding study was the significant reduction in weight gain observed in the *moringa* extract-fed mice. Healthy C57BL/6J mice fed a low fat diet (10% kcal from fat) typically gain 25-32% less weight than mice on a VHFD (25, 26). In this experiment, the *moringa* extract-fed mice gained 18% less weight than the VHFD-fed mice, demonstrating almost complete abolition of excess weight gain caused by the VHFD, without any other observable side effects. Slight differences in accumulated food intake or food aversion cannot explain the reduced weight gain in *moringa* extract-fed mice, because the ratio of accumulated food intake to body weight was actually higher in the VHFD+5% *moringa* extract-fed mice compared to the VHFD group. Previous in vitro work demonstrated MICs and MC possess anti-inflammatory activity manifested as decreased IL-1β and TNFα expression and nitric oxide (NO) production (2); effects that were also observed in this in vivo study. TNFα over-expression was previously identified as a contributing factor to obesity-induced type 2 diabetes (27), particularly by studies showing TNFα knockout mice had increased insulin sensitivity (28-30). However, only slight decreases in body weight gain were noted in these studies, indicating that the anti-inflammatory effects of MICs alone are not likely responsible for anti-obesity effects observed by *moringa* extract treatment. MICs are very effective, however, in blocking glucose production in HII4E hepatocytes, showing activity at nanomolar concentrations (FIG. 12A-B) and being close to two orders of magnitude more active than metformin (FIG. 12B). Because MICs were able to decrease PEPCK and G6P gene expression at similarly low concentrations, it is tempting to speculate that MICs act via blocking these rate-limiting steps in liver gluconeogenesis. Decreased G6P and PEPCK gene expression was also observed in liver tissue from the *moringa* extract feeding study, further supporting this mode of action (FIG. 12D). In the long term, reduced gluconeogenesis may contribute to improved insulin sensitivity, as metformin's inhibition of gluconeogenesis (31) has been a successful target for treating type 2 diabetes (32), although other studies suggest that metformin may have other modes of action (33-35). Additional symptoms of type 2 diabetes include impaired insulin sensitivity and increased serum levels of insulin, leptin, resistin, TG, and cholesterol (36-39); all of which were reduced by *moringa* extract treatment.

Collectively, the results of in vitro and in vivo experiments establish that MICs are the primary biologically active anti-obesity and anti-diabetes constituents of *moringa* extract, and the primary mechanism of action of the extract is the inhibition of liver gluconeogenesis, which directly or indirectly results in systemically increased insulin sensitivity. These effects are expected, in turn, to reduce lipid accumulation in the liver and body. These conclusions, combined with previous data on MICs anti-inflammatory effects (2), indicate that *moringa* extract and MICs have beneficial effects for the prevention and treatment of metabolic disorders such as obesity and diabetes.

Documents referenced in Example 7.
1. Mbikay M. Therapeutic potential of *Moringa oleifera* leaves in chronic hyperglycemia and dyslipidemia: a review. Front Pharmacol. 2012; 3:1-12.
2. Waterman C, Cheng D M, Rojas-Silva P, Poulev A, Dreifus J, Lila M A, et al. Stable, water extractable isothiocyanates from *Moringa oleifera* leaves attenuate inflammation in vitro. Phytochem. 2014; 103:114-22.
3. Cheenpracha S, Park E-J, Yoshida W Y, Barit C, Wall M, Pezzuto J M, et al. Potential anti-inflammatory phenolic glycosides from the medicinal plant *Moringa* oleifera fruits. Bioorgan Med Chem. 2010; 18(17):6598-602.
4. Bae J Y, Lim S S, Kim S J, Choi J S, Park J, Ju S M, et al. Bog blueberry anthocyanins alleviate photoaging in ultraviolet-B irradiation-induced human dermal fibroblasts. Mol Nutr Food Res. 2009; 53(6):726-38.
5. Brunelli D, Tavecchio M, Falcioni C, Frapolli R, Erba E, Iori R, et al. The isothiocyanate produced from glucomoringin inhibits NF-kB and reduces myeloma growth in nude mice in vivo. Biochem Pharmacol. 2010; 79(8): 1141-8.
6. Faizi S, Siddiqui B S, Saleem R, Siddiqui S, Aftab K, Gilani A H. Isolation and structure elucidation of new nitrile and mustard oil glycosides from *Moringa oleifera* and their effect on blood pressure. J Nat Prod. 1994; 57(9):1256-61.
7. Shapiro T A, Fahey J W, Wade K L, Stephenson K K, Talalay P. Chemoprotective glucosinolates and isothiocyanates of broccoli sprouts metabolism and excretion in humans. Cancer Epidem Biomar. 2001; 10(5):501-8.
8. Higdon J V, Delage B, Williams D E, Dashwood R H. Cruciferous vegetables and human cancer risk: epidemiologic evidence and mechanistic basis. Pharmacol Res. 2007; 55(3):224-36.
9. Verhoeven D T, Goldbohm R A, van Poppel G, Verhagen H, van den Brandt A. Epidemiological studies on *brassica* vegetables and cancer risk. Cancer Epidem Biomar. 1996; 5(9):733-48.
10. Traka M, Mithen R. Glucosinolates, isothiocyanates and human health. Phytochem Rev. 2009; 8(1):269-82.
11. Mirmiran P, Bahadoran Z, Hosseinpanah F, Keyzad A, Azizi F. Effects of broccoli sprout with high sulforaphane concentration on inflammatory markers in type 2 diabetic patients: A randomized double-blind placebo-controlled clinical trial. J Funct Foods. 2012; 4(4):837-41.
12. Bahadoran Z, Tohidi M, Nazeri P, Mehran M, Azizi F, Mirmiran P. Effect of broccoli sprouts on insulin resistance in type 2 diabetic patients: a randomized double-blind clinical trial. Int J Food Sci Nutr. 2012; 63(7):767-71.
13. Bahadoran Z, Mirmiran P, Azizi F. Potential Efficacy of Broccoli Sprouts as a Unique Supplement for Management of Type 2 Diabetes and Its Complications. J Med Food. 2013.
14. Wu H, Liang H, Yuan Q, Wang T, Yan X. Preparation and stability investigation of the inclusion complex of sulforaphane with hydroxypropyl-β-cyclodextrin. Carbohyd Polym. 2010; 82(3):613-7.
15. Park E-J, Cheenpracha S, Chang L C, Kondratyuk T P, Pezzuto J M. Inhibition of lipopolysaccharide-induced cyclooxygenase-2 and inducible nitric oxide synthase expression by 4-[(2'-O-acetyl-α-rhamnosyloxy)benzyl] isothiocyanate from *Moringa oleifera*. Nutr Cancer. 2011; 63(6):971-82.
16. Shetty P. Public health: India's diabetes time bomb. Nature. 2012; 485(7398):S14-S6.
17. Mbanya J C N, Motala A A, Sobngwi E, Assah F K, Enoru S T. Diabetes in sub-Saharan Africa. Lancet. 2010; 375 (9733):2254-66.
18. Ng M, Fleming T, Robinson M, Thomson B, Graetz N, Margono C, et al. Global, regional, and national prevalence of overweight and obesity in children and adults during 1980-2013: a systematic analysis for the Global Burden of Disease Study 2013. Lancet. 2014.doi:10.1016/ 50140-6736(14)60460-8
19. Folch J, Lees M, Sloane-Stanley G. A simple method for the isolation and purification of total lipids from animal tissues. J Biol Chem. 1957; 226(1):497-509.
20. Schmittgen T D, Livak K J. Analyzing real-time PCR data by the comparative C T method. Nature Protocols. 2008; 3(6):1101-8.
21. Cheng D M, Kuhn P, Poulev A, Rojo L E, Lila M A, Raskin I. In vivo and in vitro antidiabetic effects of aqueous cinnamon extract and cinnamon polyphenol-enhanced food matrix. Food Chem. 2012; 135(4):2994-3002.
22. Mosmann T. Rapid colorimetric assay for cellular growth and survival: application to proliferation and cytotoxicity assays. J Immunol Methods. 1983; 65(1):55-63.
23. Jaiswal D, Kumar Rai P, Kumar A, Mehta S, Watal G. Effect of *Moringa oleifera* Lam. leaves aqueous extract therapy on hyperglycemic rats. J Ethnopharmacol. 2009; 123(3):392-6.
24. Ndong Moussa U M, Katsumata Shin-ichi, Suzuki Kazuharu Effects of Oral Administration of *Moringa oleifera* Lam on Glucose Tolerance in Goto-Kakizaki and Wistar Rats. J Clin Biochem Nutr. 2007; 40(3):229-33.
25. Miller R S, Becker K G, Prabhu V, Cooke D W. Adipocyte gene expression is altered in formerly obese mice and as a function of diet composition. J Nutr. 2008; 138(6):1033-8.
26. Korda M, Kubant R, Patton S, Malinski T. Leptin-induced endothelial dysfunction in obesity. Am J Physiol-Heart C. 2008; 295(4):H1514-H21.
27. Moller D E. Potential role of TNF-alpha in the pathogenesis of insulin resistance and type 2 diabetes. Trends Endocrin Met. 2000; 11(6):212-7.
28. Uysal K T, Wiesbrock, S. M., Marino, M. W., Hotamisligil, G. S. Protection from obesity-induced insulin resistance in mice lacking TNFalpha function. Nature. 1997; 389:610-4.

29. Schreyer S A, Chua Jr S C, LeBoeuf R C. Obesity and diabetes in TNF-alpha receptor-deficient mice. J Clinl Invest. 1998; 102(2):402.
30. Hotamisligil G S, Murray D L, Choy L N, Spiegelman B M. Tumor necrosis factor alpha inhibits signaling from the insulin receptor. PNAS. 1994; 91(11):4854-8.
31. Hundal R S, Krssak M, Dufour S, Laurent D, Lebon V, Chandramouli V, et al. Mechanism by which metformin reduces glucose production in type 2 diabetes. Diabetes. 2000; 49(12):2063-9.
32. Knowler W C, Barrett-Connor E, Fowler S E, Hamman R F, Lachin J M, Walker E A, et al. Reduction in the incidence of type 2 diabetes with lifestyle intervention or metformin. New Engl J Med. 2002; 346(6):393-403.
33. Rena G, Pearson E R, Sakamoto K. Molecular mechanism of action of metformin: old or new insights? Diabetologia. 2013; 56(9):1898-906.
34. Geerling J J, Boon M R, van der Zon G C, van den Berg S A, van den Hoek A M, Lombès M, et al. Metformin lowers plasma triglycerides by promoting VLDL-triglyceride clearance by brown adipose tissue in mice. Diabetes. 2013; 63(3):880-91.
35. Madiraju A K, Erion D M, Rahimi Y, Zhang X-M, Braddock D T, Albright R A, et al. Metformin suppresses gluconeogenesis by inhibiting mitochondrial glycerophosphate dehydrogenase. Nature. 2014; 510:542-6.
36. Widjaja A, Stratton I M, Horn R, Holman R R, Turner R, Brabant G. UKPDS 20: plasma leptin, obesity, and plasma insulin in type 2 diabetic subjects. J Clin Endocrinol Metab. 1997; 82(2):654-7.
37. Steppan C M, Bailey S T, Bhat S, Brown E J, Banerjee R R, Wright C M, et al. The hormone resistin links obesity to diabetes. Nature. 2001; 409(6818):307-12.
38. Srinivasan K, Viswanad B, Asrat L, Kaul C, Ramarao P. Combination of high-fat diet-fed and low-dose streptozotocin-treated rat: a model for type 2 diabetes and pharmacological screening. Pharmacol Res. 2005; 52(4):313-20.
39. El Messaoudi S, Rongen G A, de Boer R A, Riksen N P. The cardioprotective effects of metformin. Current Opin Lipidol. 2011; 22(6):445-53.

Example 8—Preparation of Extracts from Seeds of a *M. oleifera* Plant

*Moringa* seeds were ground to a fine powder and subjected to the extraction protocols listed below in Table 2. Insoluble seed material was separated from the liquid extract by filtration or centrifugation and dried under vacuum to produce final extract. The amounts of recovered *moringa* isothiocyanates (MICs) were determined using HPLC and MIC-1 as a standard.

TABLE 2

| Extraction Methods | Wt of extracted seeds (g) | Total extraction vol. (ml) | Extract vol. recovered (ml) | Conc. MIC-1 in recovered extract (mg/ml) | Amount of MIC-1 recovered from seeds (mg/g) | Dry Weight of Extract (mg) | MIC conce. in the extract (%) - calculated* | MIC conc. in the extract (%) - Actual* |
|---|---|---|---|---|---|---|---|---|
| Dry seeds ground to a fine powder. Extracted for 60 minutes in 50 ml of 100% water. After incubation, 200 ml of 95% ethanol was added. | 25.1 | 250.91 | 198 | 3.1 | 24.5 | 1908 | 32.2 | 24 |
| Dry seeds ground to a fine powder. Extracted for 30 min in 3 ml of water. After incubation, 7 ml of 95% ethanol was added. | 1 | 10 | 7 | 2.80 | 19.60 | 107.8 | 18.2 | 12.7 |
| Dry seeds ground to a fine powder. Extracted for 30 min in 2 ml of 100% water. After incubation, 8 ml of 95% ethanol was added. | 1 | 10 | 7 | 2.40 | 16.80 | 92.7 | 18.1 | 10.6 |
| Dry seeds ground to a fine powder. Extracted for 30 minutes in 2 ml of 100% water. After incubation, 4 ml of 95% ethanol was added. | 1 | 6 | 3.5 | 4.10 | 14.35 | 78.1 | 18.4 | 9.0 |
| Seeds ground to a fine powder in water and extracted for 30 minutes. | 2 | 16 | 7 | 2.86 | 10.01 | 178.3 | 11.2 | 5.3 |
| Dry seeds ground to a fine powder and then extracted for 30 minutes in 100% water | 1 | 8 | 4.75 | 2.68 | 12.73 | 130.7 | 9.7 | 5.0 |

TABLE 2-continued

| Extraction Methods | Wt of extracted seeds (g) | Total extraction vol. (ml) | Extract vol. recovered (ml) | Conc. MIC-1 in recovered extract (mg/ml) | Amount of MIC-1 recovered from seeds (mg/g) | Dry Weight of Extract (mg) | MIC conce. in the extract (%) - calculated* | MIC conc. in the extract (%) - Actual* |
|---|---|---|---|---|---|---|---|---|
| Dry seeds ground to a fine powder and extracted for 30 minutes in 40% ethanol. | 1 | 8 | 3.5 | 1.00 | 3.50 | 67.3 | 5.2 | 5.1 |
| Dry seeds ground to a fine powder and extracted for 30 min 50% ethanol. | 1 | 10 | 2 | 0.85 | 1.70 | 16.4 | 10.4 | 5.6 |
| Dry seeds ground to a fine powder. Extracted for 30 minutes in 70% ethanol | 1 | 8 | 4.5 | 0.81 | 3.65 | 74.3 | 4.9 | 1.1 |
| Seeds ground to a fine powder in 70% ethanol and extracted for 30 minutes | 2 | 16 | 5.25 | 0.40 | 1.05 | 153 | 1.4 | 0.53 |
| Dry seeds ground to a fine powder and extracted for 30 min in 10 ml of 95% ethanol. | 1 | 10 | 5 | Not detectable | Not detectable | 18.8 | Not detectable | Not detectable |

*Actual concentration are lower than calculated concentrations because of MICs loss and/or degradation during drying.

The data provided in Table 2 demonstrates that incubating injured (e.g., ground) seeds in a solution comprising water, or injuring seeds in a solution comprising water produces optimal conditions for activating myrosinase and forming MICs. Adding solvent (e.g., ethanol) to the injured seeds before or with a solution comprising water progressively inhibited formation of MICs. No detectable MICs were formed when 95% ethanol was directly added to the injured seeds or seeds that were injured in the presence of 95% ethanol.

As shown in Table 2, 95% ethanol was most effective in extracting MICs from seeds that were injured in a solution comprising water (or injured seeds that were incubated in a solution comprising water for a period of time before addition of the ethanol), primarily because it allowed most rapid drying of the extract. Differences between calculated and actual concentration of MICs in the extract can be explained by losses that occurred during the drying process. Long drying time of the samples with high water content resulted in significant losses on MIC from the final extract. Much faster drying times for samples with high ethanol concentration resulted in lower loss of MICs.

In summary, initial incubation of the injured seeds in a solution comprising water prior to extraction with ethanol was sufficient to activate myrosinase and convert most moringa glucosinolates into MICs, as confirmed by the HPLC analysis. MICs formed in this initial process can be effectively extracted in ethanol or other solvents. However, once MICs are formed as a result of adding a solution comprising water to the injured seeds, ethanol can be added to increase the extraction volume and to facilitate extraction efficiency. It is important to note that MIC-1 is the major isothiocyanates formed in moringa seeds and that other isothiocyanates are formed only in trace amounts. The data provided herein demonstrates that injuring seeds in a solution comprising water (e.g., 1:1 to 1:3 seed to water ratio w/w) for 30-60 minutes followed by extraction with 95% ethanol or other solvent appropriate for solubilizing MICs is an effective way of producing moringa seed extracts enriched in MICs.

Numerous modifications and variations in the practice of the invention are expected to occur to those of skill in the art upon consideration of the presently preferred embodiments thereof. Consequently, the only limitations which should be placed upon the scope of the invention are those which appear in the appended claims.

All of the U.S. patents, U.S. patent application publications, U.S. patent applications, foreign patents, foreign patent applications and non-patent publications referred to in this specification and/or listed in the Application Data Sheet, are incorporated herein by reference, in their entireties or in relevant part, as would be apparent from the context of their citation.

From the foregoing it will be appreciated that, although specific embodiments of the invention have been described herein for purposes of illustration, various modifications may be made without deviating from the spirit and scope of the invention.

REFERENCES

Alberti et al., (2009). Circulation, 120(16), 1640-1645.
Amaglo et al., (2010). Food Chemistry, 122(4), 1047-1054.
Bao et al., (2011). Biochimica et Biophysica Acta—Reviews on Cancer, 1815(2), 135-146.
Bennett et al., (2003), Journal of Agricultural and Food Chemistry, 51(12), 3546-3553.
Bhargava, P., & Lee, C. (2012), Biochemical Journal, 442, 253-262.
Brunelli et al., 2010), Biochemical Pharmacology, 79(8), 1141-1148.
Cheenpracha et al., (2010), Bioorganic & Medicinal Chemistry, 18(17), 6598-6602.
Dillard, C. J., & German, J. B. (2000), Journal of the Science of Food and Agriculture, 80(12), 1744-1756.

Eylen et al., (2008), Journal of Food Engineering, 89(2), 178-186.
Fahey, J. W. (2005), Trees for Life Journal 1, 5.
Ferrante, A. W. (2007), Journal of Internal Medicine, 262(4), 408-414.
Force et al., (2007), Postharvest Biology and Technology, 44(2), 175-178.
Franklin et al., (2013), Drug Development and Industrial Pharmacy, 0, 1-9.
Gallaher et al., (2012), Journal of Agricultural and Food Chemistry, 60(6), 1358-1362.
Geronikaki, A. A., & Gavalas, A. M. (2006), Combinatorial Chemistry & High Throughput Screening, 9(6), 425-442.
Giusti, M. M., & Wrolstad, R. E. (2003), Biochemical Engineering Journal, 14(3), 217-225.
Hobbs et al., (1999), Annual Review of Pharmacology and Toxicology, 39(1), 191-220.
Hotamisligil et al., (1994), Proceedings of the National Academy of Sciences, 91(11), 4854-4858.
Mariappan et al., (2010), Cardiovascular Research, 85(3), 473-483.
Mbikay, M. (2012), Frontiers in Pharmacology, 3, 1-12.
Mirza et al., (2012), Cytokine, 57(1), 136-142.
Mocellin, S., & Nitti, D. (2008), Frontiers in Bioscience, 13, 2774-2783.
Mosmann, T. (1983), Journal of Immunological Methods, 65(1), 55-63.
Moyo et al., (2012), Meat Science, 91(4), 441-447.
Pandey et al., (2012), Medicinal & Aromatic Plants: Open Access, 1, 1-8.
Park et al., (2011), Nutrition and Cancer, 63(6), 971-982.
Pereira et al., (2002), Journal of Agricultural and Food Chemistry, 50(21), 6239-6244.
Prior et al., (2003), Journal of Agricultural and Food Chemistry, 51(11), 3273-3279.
Siddhuraju, P., & Becker, K. (2003), Journal of Agricultural and Food Chemistry, 51(8), 2144-2155.
Singleton, V., & Rossi, J. A. (1965), American Journal of Enology and Viticulture, 16(3), 144-158.
Song, L., & Thornalley, P. J. (2007), Food and Chemical Toxicology, 45(2), 216-224.
Sreelatha, S., & Padma, P. R. (2009), Plant Foods for Human Nutrition, 64(4), 303-311.
Srivastava, S. K., & Singh, S. V. (2004), Carcinogenesis, 25(9), 1701-1709.
Traka, M., & Mithen, R. (2009). Glucosinolates, isothiocyanates and human health. Phytochemistry Reviews, 8(1), 269-282.
Vongsak et al., (2012), Industrial Crops and Products, 44, 566-571.
Wadsworth, T. L., & Koop, D. R. (1999), Biochemical Pharmacology, 57(8), 941-949.
Wang, Y., & Beydoun, M. A. (2007), Epidemiologic Reviews, 29(1), 6-28.
Wu et al., (2004). Lipophilic and hydrophilic antioxidant capacities of common foods in the United States. Journal of Agricultural and Food Chemistry, 52(12), 4026-4037.
Xu C et al., (2005), Oncogene 24, 4486-4495.
Xu et al., (2003), The Journal of Clinical Investigation, 112(12), 1821-1830.

What is claimed is:

1. A method of extracting *Moringa isothiocyanates* (MICs) from seeds of an *M. oleifera* plant comprising:
   (a) incubating injured seeds from the plant in a solvent consisting of water at a ratio of between 1:2 to 1:10 weight of the injured seeds to volume of water (w/v) for 30 to 60 minutes at a temperature of 22°-80° C.; and
   (b) adding an extraction solvent comprising a C1-C4 alcohol to the water after (a) in an amount ranging from 1:5 to about 1:20 (w/v; weight injured seeds to volume of extraction solvent) to extract the MICs from the seeds of the *M. oleifera* plant and extracting for a sufficient duration to produce the extract containing the MICs.

2. The method of claim 1, wherein the injured seeds are incubated in water 1:1 to about 1:4 weight of injured seed to volume of water ratio (w/v).

3. The method of claim 1, wherein the incubating step is performed at room temperature.

4. The method of claim 1, wherein the extraction solvent is 95% ethanol.

* * * * *

UNITED STATES PATENT AND TRADEMARK OFFICE
CERTIFICATE OF CORRECTION

PATENT NO. : 11,147,847 B2
APPLICATION NO. : 14/683730
DATED : October 19, 2021
INVENTOR(S) : Ilya Raskin et al.

Page 1 of 1

It is certified that error appears in the above-identified patent and that said Letters Patent is hereby corrected as shown below:

In the Specification

Please insert the below title and paragraph in Column 1, Line 16:
--STATEMENT OF GOVERNMENT SUPPORT
This invention was made with government support under grant number AT002776 awarded by the National Institutes of Health. The government has certain rights in the invention.--

Signed and Sealed this
Eleventh Day of March, 2025

Coke Morgan Stewart
*Acting Director of the United States Patent and Trademark Office*

SEQUENCE LISTING

<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: Synthetic primer

<400> SEQUENCE: 1
aaccgtgaaa agatgaccca gat                                              23

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
cacagcctgg atggctacgt                                                  20

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
caaccaacaa gtgatattct ccat                                             24

<210> SEQ ID NO 4
<211> LENGTH: 21

```
<212> TYPE: DNA
<213> ORGANISM: Artificial Sequence
<220> FEATURE:
<223> OTHER INFORMATION: Synthetic primer

<400> SEQUENCE: 4
gatccacact ctccagctgc a                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
ccctcctgat cttgtgttgg a                                              21

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
tcaacccgag ctcctggaa                                                 19

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
tggtgcctgg tctgatgatg                                                20

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
gtggtaaccg ctcaggtgtt g                                              21

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
tgggagtaga caaggtacaa ccc                                            23

<210> SEQ ID NO 10
<211> LENGTH: 25
<212> TYPE: DNA
<213> ORGANISM: Artificial Sequence
<220> FEATURE:
<223> OTHER INFORMATION: Synthetic primer

<400> SEQUENCE: 10
```

```
catcttctca aaattcgagt gagaa                                    25

<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11
tcggaggctt aattacacat gttc                                     24

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
tgccattgca caactctttt ct                                       22
```